(12) United States Patent
Rangan

(10) Patent No.: US 12,168,513 B2
(45) Date of Patent: Dec. 17, 2024

(54) MITIGATING OPERATIONAL RISK IN AIRCRAFT

(71) Applicant: Federal Express Corporation, Memphis, TN (US)

(72) Inventor: Suresh Rangan, Frisco, TX (US)

(73) Assignee: Federal Express Corporation, Memphis, TN (US)

(*) Notice: Subject to any disclaimer, the term of this patent is extended or adjusted under 35 U.S.C. 154(b) by 0 days.

(21) Appl. No.: 18/304,793

(22) Filed: Apr. 21, 2023

(65) Prior Publication Data

US 2023/0356842 A1 Nov. 9, 2023

Related U.S. Application Data

(62) Division of application No. 16/818,720, filed on Mar. 13, 2020, now Pat. No. 11,661,195.
(Continued)

(51) Int. Cl.
*B64D 11/00* (2006.01)
*A61B 5/16* (2006.01)
(Continued)

(52) U.S. Cl.
CPC .............. *B64D 11/00* (2013.01); *A61B 5/163* (2017.08); *A61B 5/18* (2013.01); *G06F 1/163* (2013.01);
(Continued)

(58) Field of Classification Search
CPC .......... B64D 11/00; A61B 5/163; A61B 5/18; G06F 16/9035; G06F 1/163; G06V 20/597; G06V 40/18; G08B 21/06; G08G 5/003
(Continued)

(56) References Cited

U.S. PATENT DOCUMENTS

| 5,433,223 A | 7/1995 | Moore-Ede et al. |
| 6,289,277 B1 | 9/2001 | Feyereisen et al. |

(Continued)

FOREIGN PATENT DOCUMENTS

| CN | 104616436 | 5/2015 |
| EP | 2278508 | 1/2011 |

(Continued)

OTHER PUBLICATIONS

Blom, et al., "Accident risk assessment for advanced air traffic management," National Aerospace Laboratory NLR, NLR-TP-2001-642, retrieved from URL <http://reports.nlr.nl/xmlui/bitstream/handle/10921/8O7/TP-2OO1-642.pdf?sequence=1>, Dec. 31, 2001, 27 pages.
(Continued)

*Primary Examiner* — Zhen Y Wu
(74) *Attorney, Agent, or Firm* — Fish & Richardson P.C.

(57) ABSTRACT

An in-flight risk management system includes an eye sensor, a seat sensor, and one or more in-flight risk management computers that perform operations including: obtaining history information for a flight crew member, obtaining flight information associated with a flight on which the flight crew member will be present, determining, based on the history information and the flight information, a predicted fatigue profile for the flight crew member, determining, based on the predicted fatigue profile for the crew member, one or more fatigue indicator profiles for the flight crew member, obtaining, from at least one of the eye sensor or seat sensor, one or more measured fatigue indicator values associated with the flight crew member, generating, based on the one or more measured fatigue indicator values, one or more updated fatigue indicator profiles, and generating, based on the one or more updated fatigue indicator profiles, an updated predicted fatigue profile.

22 Claims, 14 Drawing Sheets

Related U.S. Application Data

(60) Provisional application No. 62/817,932, filed on Mar. 13, 2019.

(51) Int. Cl.
  *A61B 5/18* (2006.01)
  *G06F 1/16* (2006.01)
  *G06F 16/9035* (2019.01)
  *G06V 20/59* (2022.01)
  *G06V 40/18* (2022.01)
  *G08B 21/06* (2006.01)
  *G08G 5/00* (2006.01)

(52) U.S. Cl.
  CPC ........ *G06F 16/9035* (2019.01); *G06V 20/597* (2022.01); *G06V 40/18* (2022.01); *G08B 21/06* (2013.01); *G08G 5/003* (2013.01)

(58) Field of Classification Search
  USPC .......................................................... 701/3
  See application file for complete search history.

(56) References Cited

U.S. PATENT DOCUMENTS

| | | |
|---|---|---|
| 6,480,770 B1 | 11/2002 | Wischmeyer |
| 6,940,426 B1 | 9/2005 | Vaida |
| 7,118,530 B2 | 10/2006 | Hursh et al. |
| 7,324,954 B2 | 1/2008 | Calderaro et al. |
| 7,435,227 B2 * | 10/2008 | Farbos ................... G08B 21/06 |
| | | 340/576 |
| 7,898,426 B2 | 3/2011 | Rai et al. |
| 8,554,459 B2 | 10/2013 | Johnson et al. |
| 8,665,121 B2 | 3/2014 | Shavit |
| 8,843,303 B1 | 9/2014 | Young et al. |
| 9,540,118 B2 | 1/2017 | Rangan et al. |
| 9,613,543 B2 * | 4/2017 | Whitlow ............ B64D 45/0015 |
| 9,771,081 B2 * | 9/2017 | Grube ................... B60W 40/08 |
| 10,053,227 B2 | 8/2018 | Rangan et al. |
| 10,116,378 B1 * | 10/2018 | Morowsky ........... G08G 5/0013 |
| 10,431,215 B2 * | 10/2019 | Cohen ..................... G06F 3/012 |
| 10,952,668 B2 * | 3/2021 | Ruwe ...................... A61B 5/318 |
| 2002/0005784 A1 | 1/2002 | Balkin et al. |
| 2003/0065428 A1 | 4/2003 | Mendelson et al. |
| 2003/0225856 A1 | 12/2003 | Pietrowski et al. |
| 2004/0199445 A1 | 10/2004 | Eder |
| 2005/0149852 A1 | 7/2005 | Bleicher et al. |
| 2005/0256682 A1 | 11/2005 | Galutia et al. |
| 2006/0287779 A1 * | 12/2006 | Smith ....................... A61B 5/18 |
| | | 701/1 |
| 2007/0208278 A1 * | 9/2007 | Kohen-Raz .......... A61B 5/4023 |
| | | 600/595 |
| 2008/0215407 A1 | 9/2008 | Pachon et al. |
| 2008/0238694 A1 * | 10/2008 | Ishida ..................... A61B 5/163 |
| | | 340/575 |
| 2009/0204453 A1 | 8/2009 | Cooper et al. |
| 2010/0145552 A1 | 6/2010 | Herman et al. |
| 2011/0071873 A1 | 3/2011 | Vaughan et al. |
| 2012/0075122 A1 * | 3/2012 | Whitlow ............ B64D 45/0056 |
| | | 340/963 |
| 2012/0116610 A1 * | 5/2012 | Righi ..................... G05D 1/0061 |
| | | 244/76 R |
| 2012/0203464 A1 | 8/2012 | Mollicone et al. |
| 2012/0232414 A1 | 9/2012 | Mollicone et al. |
| 2012/0242819 A1 * | 9/2012 | Schamp ................ G06V 20/597 |
| | | 348/78 |
| 2013/0268146 A1 * | 10/2013 | Baudry ................... G01C 23/00 |
| | | 701/3 |
| 2014/0081179 A1 * | 3/2014 | Moore-Ede ............ G16H 50/30 |
| | | 600/595 |
| 2014/0187871 A1 | 7/2014 | Carrazo et al. |
| 2014/0362202 A1 * | 12/2014 | Tschirhart ............ G06V 40/165 |
| | | 348/78 |
| 2015/0123820 A1 * | 5/2015 | Merle ...................... A61B 5/18 |
| | | 340/945 |
| 2015/0148616 A1 * | 5/2015 | Van Dongen .......... G16H 40/63 |
| | | 600/300 |
| 2015/0164400 A1 * | 6/2015 | Shimizu ................. G08B 21/06 |
| | | 600/513 |
| 2015/0193664 A1 * | 7/2015 | Marti ..................... G08B 21/06 |
| | | 382/103 |
| 2015/0194035 A1 * | 7/2015 | Akiva ..................... H04N 7/183 |
| | | 340/575 |
| 2015/0251771 A1 * | 9/2015 | Whitlow .............. G08G 5/0021 |
| | | 701/3 |
| 2016/0004969 A1 | 1/2016 | Cetinich et al. |
| 2016/0048658 A1 * | 2/2016 | Rangan .................. G16H 15/00 |
| | | 702/19 |
| 2016/0071393 A1 * | 3/2016 | Kaplan .................. A61B 5/162 |
| | | 340/539.12 |
| 2016/0090097 A1 * | 3/2016 | Grube ................... B60W 40/08 |
| | | 340/576 |
| 2016/0092825 A1 * | 3/2016 | Zimmer ........... G06Q 10/06311 |
| | | 705/7.16 |
| 2016/0130013 A1 * | 5/2016 | Rangan .................. G08G 5/003 |
| | | 340/963 |
| 2016/0299506 A1 * | 10/2016 | Bruggeman ........... G05D 1/106 |
| 2017/0081041 A1 | 3/2017 | Rangan et al. |
| 2017/0210483 A1 | 7/2017 | Hamblin et al. |
| 2017/0334456 A1 * | 11/2017 | Deligianni ............... A61B 5/18 |
| 2017/0336789 A1 * | 11/2017 | Sane .................. G06Q 10/0631 |
| 2018/0178808 A1 * | 6/2018 | Zhao .................... B60K 28/066 |
| 2019/0009923 A1 | 1/2019 | Rangan et al. |
| 2019/0061772 A1 * | 2/2019 | Prinz ...................... B60K 28/06 |
| 2019/0340556 A1 * | 11/2019 | Whitlow .................. G06F 3/167 |
| 2020/0261017 A1 * | 8/2020 | Ruwe ...................... A61B 5/18 |
| 2021/0204868 A1 * | 7/2021 | Ruwe ................. A61B 5/14551 |
| 2022/0230522 A1 * | 7/2022 | Myers ..................... A61B 5/18 |

FOREIGN PATENT DOCUMENTS

| | | |
|---|---|---|
| EP | 2434465 | 3/2012 |
| EP | 3001366 | 3/2016 |
| EP | 3218855 | 9/2017 |
| EP | 3343306 | 7/2018 |
| JP | 2001256598 | 9/2001 |
| JP | 2012048310 | 3/2012 |
| JP | 2014151910 | 8/2014 |
| WO | WO 2013162839 | 10/2013 |
| WO | WO 2014066059 | 5/2014 |
| WO | WO 2016028228 | 2/2016 |
| WO | WO 2016077024 | 5/2016 |

OTHER PUBLICATIONS

Blom, et al., "Collision risk modeling of air traffic," European Control Conference (ECC), Sep. 1-4, 2003, Cambridge, UK, pp. 2236-2241.

Dexter, "Pilot Fatigue Study: A First Look," Biological Clocks and Shift Work Scheduling, Hearings before the subcommittee on Investigations and oversight of the committee on science and technology house of representatives, Mar. 23-24, 1983, pp. 68-69.

Fletcher and Dawson, "A predictive model of work-related fatigue based on hours of work," Journal of Occupational Health and Safety—Australia and New Zealand, 1997, 13(5):471-485.

International Preliminary Report on Patentability in International Appln. No. PCT/US2020/022631, dated Sep. 23, 2021, 12 pages.

International Search Report and Written Opinion in International Application No. PCT/US2020/022631, dated Sep. 15, 2020, 20 pages.

Invitation to Pay Additional Fees in International Application No. PCT/US2020/022631, dated Jul. 24, 2020, 12 pages.

Miyamoto et al., "Healthcare technology for realizing a healthy and lively society—Wearable Sensors Corresponding to Various Applications in Healthcare Field", Toshiba Review, Japan, Toshiba corporation, Nov. 1, 2014, vol. 69, No. 11, 7 pages (publication showing well-known technology) [No English version available].

(56) References Cited

OTHER PUBLICATIONS

Signal, et al., "Sleep Measurement in Flight Crew: Comparing Actigraphic and Subjective Estimates to Polysomnography," Aviat. Space Environ, Med., 2005,76(11):1058-63.

Triantaphyllou, et al., "Using The Analytic Hierarchy Process For Decision Making In Engineering Applications: Some Challenges," International Journal of Industrial Engineering: Applications and Practice, 1995, 2(1):35-44.

U.S. Department of Transportation, Federal Aviation Administration, "Flight Risk Assessment Tool," Information for Operators, InFO 07015, Jul. 3, 2007, 5 pages.

U.S. Department of Transportation, Federal Aviation Administration, FAA/Industry Training Standards, Personal and Weather Risk Assessment Guide, Version 1.0, Oct. 2003, 18 pages.

* cited by examiner

MITIGATING OPERATIONAL RISK IN AIRCRAFT

CROSS-REFERENCE TO RELATED APPLICATIONS

This application is a divisional of U.S. patent application Ser. No. 16/818,720, entitled "Mitigating Operational Risk In Aircraft," filed Mar. 13, 2020, which claims the benefit under 35 U.S.C. § 119(e) of U.S. Provisional Patent Application No. 62/817,932, entitled "Operator Fatigue Assessment," filed Mar. 13, 2019, which are incorporated herein by reference in their entirety.

TECHNICAL FIELD

This disclosure is generally directed to aircraft flight control systems and processes for mitigating in-flight operational risks due to pilot fatigue. Implementations include processes and systems directed to automated and remote aircraft control. Some processes and systems described herein can also be implemented in control systems of vehicles including trains, ships, and automobiles.

BACKGROUND

This disclosure relates generally to electronic systems and more particularly to systems for evaluating risks related to operator fatigue during flight. The risks associated with operator fatigue during a flight are numerous and severe. However, monitoring the fatigue levels of flight crew members is logistically challenging, as flight crew members (e.g., pilots) often lack the ability to effectively measure their own levels of fatigue or fail to report signs of fatigue. Consequently, comprehensive, real-time monitoring of operator fatigue during a flight is not usually available.

SUMMARY

This specification generally relates to methods for monitoring and mitigating flight risk. Implementations include processes and systems directed to automated and remote aircraft control. Some processes and systems described herein can also be implemented in control systems of vehicles including trains, ships, and automobiles.

Implementations of the present disclosure generally provide a method and systems for determining operator fatigue and that can be designed to reduce flight risk by evaluating the fatigue level of one or more flight crew members (e.g., pilots) in real-time based on comprehensive and interrelated sets of fatigue indicators. For example, a pilot's expected level of fatigue throughout a flight can be predicted based on a variety of related risk factors and fatigue indicators, and, in response, flight risk mitigation interventions can be provided to reduce the flight risk posed by the pilot's predicted fatigue levels.

In some implementations, actions include obtaining history information for a flight crew member, the history information including data that is representative of rest and wake activity of the flight crew member over a period of time, obtaining flight information associated with a flight on which the flight crew member will be present, the flight information indicating a series of expected events during the flight, determining, based on the history information and the flight information, a predicted fatigue profile for the flight crew member, determining, based on the predicted fatigue profile for the flight crew member, one or more fatigue indicator profiles for the flight crew member, the one or more fatigue indicator profiles representing expected values of one or more respective measureable fatigue indicators, obtaining, from at least one sensor in an aircraft, one or more measured fatigue indicator values associated with the flight crew member, generating, based on the one or more measured fatigue indicator values, one or more updated fatigue indicator profiles, and generating, based on the one or more updated fatigue indicator profiles, an updated predicted fatigue profile. Other implementations, of this aspect include corresponding systems, apparatus, and computer programs, configured to perform the actions of the methods, encoded on computer storage devices.

These and other implementations can each optionally include one or more of the following features: history information includes flight history data for the flight crew member; determining the predicted fatigue profile includes determining, based on the flight history data for the flight crew member, a sleep history for the flight crew member, and determining, based on the sleep history for the flight crew member, a predicted level of fatigue for the flight crew member for an estimated flight time of the flight; determining, based on the flight history data for the flight crew member, a sleep history for the flight crew member includes processing the flight history data using a model that correlates flight history data and sleep; determining the predicted level of fatigue for the flight crew member for a period of time includes applying a fatigue model that correlates sleep with expected fatigue to the sleep history for the flight crew member; the sleep history for the flight crew member includes a number of hours the flight crew member has slept in the prior 24 hours; the history information includes data related to a training history of the flight crew member; the history information includes one or more prior predicted fatigue profiles and one or more respective prior measured fatigue indicator values for the flight crew member corresponding to one or more prior flights performed by the flight crew member; the one or more fatigue indicator profiles are determined at least in part based on the one or more prior predicted fatigue profiles and the one or more respective prior measured fatigue indicator values for the flight crew member corresponding to the one or more prior flights performed by the flight crew member; the updated predicted fatigue profile is generated at least in part based on the one or more prior predicted fatigue profiles and the one or more respective prior measured fatigue indicator values for the flight crew member corresponding to the one or more prior flights performed by the flight crew member; obtaining history information for a flight crew member includes receiving the history information from a wearable smart device worn by the flight crew member; the flight information includes an estimated time of departure for the flight; the flight information includes an estimated time of arrival for the flight; the flight information includes information related to a departure airport for the flight; the flight information includes information related to an arrival airport for the flight; the flight information includes an estimated flight time; the flight information includes weather data; determining, based on the updated predicted fatigue profile, one or more updated fatigue indicator profiles; the one or more updated fatigue indicator profiles and the updated predicted fatigue profile are determined multiple times throughout the flight; determining a predicted fatigue profile includes obtaining a plurality of group fatigue profiles, selecting a group fatigue profile from the plurality of group fatigue profiles based on the history information for the flight crew member, and adjusting the selected group fatigue profile based on the flight information; the selected group fatigue profile includes an average level of fatigue for a plurality of flight crew members over a period of time; selecting a group fatigue profile from the plurality of group fatigue profiles includes comparing the history information for the flight crew member to the history information for one or more pluralities of test subjects, each of the one or more pluralities of test subjects being specific to a group fatigue profile, determining a plurality of test subjects with history information closest to the history information for the flight crew member, and selecting the group fatigue profile associated with the determined plurality of test subjects; adjusting the selected group fatigue profile based on the flight information includes altering the group fatigue profile according to an estimated flight time of the flight; generating the one or more fatigue indicator profiles for the flight crew member includes obtaining one or more correlations between one or more fatigue levels and one or more fatigue indicator values, and applying the one or more correlations to the predicted fatigue profile to generate one or more fatigue indicator profiles, each fatigue indicator profile being specific to a fatigue indicator of one or more fatigue indicators; the one or more correlations are generated based on measuring one or more fatigue indicator values for a plurality of test subjects and measuring one or more fatigue levels the plurality of test subjects; the one or more measured fatigue indicator values include at least one of an eyelid closure rate, a length of eyelid closure, a fixation of gaze measure, or an eye scanning measure; the one or more measured fatigue indicator values include at least one of a rate of leg movement or a rate of weight shifting; the one or more measured fatigue indicator values include at least one of a pulse, a blood pressure, a rate of breathing, or a body temperature; the one or more measured fatigue indicator values include an audio data; the audio data includes a rate of errors in a set of standard protocol commands; the at least one sensor includes one or more eye tracking sensors; the one or more eye tracking sensors includes one or more infrared eye tracking sensors; the at least one sensor includes one or more leg motion sensors; the one or more leg motion sensors include one or more accelerometers; the one or more leg motion sensors include one or more pressure sensors; the one or more leg motion sensors are coupled to one or more cushions of one or more seats in the aircraft; the at least one sensor includes one or more sensors for measuring human physiology outputs; the at least one sensor includes one or more wearable devices for measuring human physiology outputs; the one or more wearable devices include one or more jackets with human physiology sensors; the one or more wearable devices include one or more bracelets with human physiology sensors; the at least one sensor includes one or more audio sensors; the one or more audio sensors include one or more microphones; the one or more updated fatigue indicator profiles include a plurality of predicted fatigue indicator values for a duration of the flight; generating the one or more updated fatigue indicator profiles includes replotting the one or more fatigue indicator profiles for the flight crew member based on the one or more measured fatigue indicator values obtained from the at least one sensor; generating the one or more updated fatigue indicator profiles includes processing the one or more measured fatigue indicator values using a trained machine learning model; the one or more updated fatigue indicator profiles are generated in response to a determination that the one or more measured fatigue indicator values have deviated more than a threshold amount of deviation from the one or more fatigue indicator profiles; generating an updated predicted fatigue profile includes obtaining one or more correlations between fatigue levels and one or more fatigue indicator values, and applying the one or more correlations to the respective one or more fatigue indicator profiles to generate an update predicted fatigue profile; the one or more correlations are generated based on measuring one or more fatigue indicator values and one or more fatigue levels for a plurality of test subjects; the updated predicted fatigue profile includes one or more predicted fatigue levels for the flight crew member for a duration of the flight; the updated predicted fatigue profile is generated in response to a determination that a threshold amount of deviation has occurred between the one or measured fatigue indicator values and the one or more fatigue indicator profiles; providing, based at least partly on the updated predicted fatigue profile, one or more flight risk mitigation interventions; providing one or more flight risk mitigation interventions includes providing a warning to the flight crew member; providing one or more flight risk mitigation interventions includes automatically rerouting the flight to an alternate landing location; automatically rerouting the flight includes sending a request to the flight crew member to reroute the flight, obtaining, from the flight crew member, an acceptance of the request, and automatically rerouting a global positioning system (GPS) of the aircraft to an alternate landing location in response to obtaining the acceptance; providing the one or more flight risk mitigation interventions includes automatically engaging an autopilot function of the aircraft; automatically engaging the autopilot function of the aircraft includes sending a request to the flight crew member to automatically engage the autopilot function of the aircraft, obtaining, from the flight crew member, an acceptance of the request, and automatically engaging the autopilot function of the aircraft in response to obtaining the acceptance; providing the one or more flight risk mitigation interventions includes directing control of the aircraft from the flight crew member to a remote operator; the remote operator includes one or more ground control employees; the remote operator includes a remote pilot located at a ground-based location; the remote operator includes two or more pilots at a ground-based location; directing control of the aircraft from the flight crew member to a remote operator includes sending a request to the flight crew member to direct control of the aircraft to a remote operator, obtaining, from the flight crew member, an acceptance of the request, and automatically directing control of the aircraft to the remote operator in response to obtaining the acceptance; providing the one or more flight risk mitigation interventions includes switching control of the aircraft to a second remote operator; providing the one or more flight risk mitigation interventions includes switching the control of the aircraft from the remote operator back to the flight crew member; obtaining history information for a second flight crew member, the history information comprising data that is representative of rest and wake activity of the second flight crew member over the period of time, the second flight crew member being present on the flight, determining, based on the flight information and the history information for the second flight crew member, a predicted fatigue profile for the second flight crew member, determining, based on the predicted fatigue profile for the second flight crew member, one or more fatigue indicator profiles for the second flight crew member, the one or more fatigue indicator profiles representing expected values of one or more respective measureable fatigue indicators, obtaining, from at least one sensor in an aircraft, one or more measured fatigue indicator values associated with the second flight crew member, generating, based on the one or more measured fatigue indicator values, one or more updated fatigue indicator profiles for the second flight crew member, and generating, based on the one or more updated fatigue indicator profiles for the second flight crew member, an updated predicted fatigue profile for the second flight crew member; providing, based at least partly on the updated predicted fatigue profile for the flight crew member and the updated predicted fatigue profile for the second flight crew member, one or more flight risk mitigation interventions; the one or more flight risk mitigation interventions are provided, at least in part, based on a comparison of the updated predicted fatigue profile for the flight crew member and the updated predicted fatigue profile for the second flight crew member; providing one or more flight risk mitigation interventions includes switching control of the aircraft from the flight crew member to the second flight crew member; providing one or more flight risk mitigation interventions includes engaging an autopilot function of the aircraft; providing one or more flight risk mitigation interventions includes alerting the flight crew member to rest, and alerting the second flight crew member to control the aircraft.

In another general aspect, actions include obtaining a plurality of fatigue indicator values for each of a plurality of test subjects, obtaining a plurality of respective fatigue levels for each of the plurality of test subjects, determining one or more correlations between the plurality of fatigue indicator values and the plurality of respective fatigue levels, obtaining a plurality of fatigue indicator values for an individual flight crew member, and generating a fatigue indicator profile for the individual flight crew member based on the one or more correlations and the plurality of fatigue indicator values for the individual flight crew member.

The present disclosure also provides a system for implementing the methods provided herein. The system includes one or more processors, and one or more data stores connectable to the one or more processors and storing instructions that, when executed, cause the one or more processors to perform operations in accordance with implementations of the methods provided herein.

The present disclosure further provides a non-transitory computer-readable storage device storing software comprising instructions executable by one or more computers which, upon such execution, cause the one or more computers to perform operations in accordance with implementations of the methods provided herein.

It is appreciated that methods in accordance with the present disclosure can include any combination of the aspects and features described herein. That is, methods in accordance with the present disclosure are not limited to the combinations of aspects and features specifically described herein, but also include any combination of the aspects and features provided.

Implementations of the present disclosure provide one or more of the following technical advantages and/or technical improvements compared to previously available solutions. Implementations provide a system that enables real-time tracking of the fatigue level of a flight crew member, such as a pilot, during flight. By tracking fatigue levels of crew members during flight, heightened levels of fatigue of the flight crew members can be detected and, in response, actions to reduce the risk posed by a crew member's fatigue can be implemented. Moreover, individuals are typically not skilled at estimating their own level of fatigue, and, as a result, often fail to accurately detect when they are experiencing increased levels of fatigue By predicting the fatigue levels of crew members in real-time during flights and providing mitigations responsive to high levels of predicted fatigue, the flight risk management systems described herein improve the safety of air travel.

The details of one or more implementations of the subject matter described in this specification are set forth in the accompanying drawings and the description below. Other features, aspects, and advantages of the subject matter will become apparent from the description, the drawings, and the claims

DETAILED DESCRIPTION

In some implementations described below, a flight risk management framework is designed to reduce flight risk by evaluating the fatigue level of one or more flight crew members (e.g., one or more pilots) during a flight based on comprehensive and interrelated sets of risk factors. For example, the flight risk management framework can be configured to predict a flight crew member's expected level of fatigue throughout a flight based on a variety of related risk factors, and, in response, can provide mitigation techniques to reduce the flight risk posed by the flight crew member's fatigue level.

Figure 1:
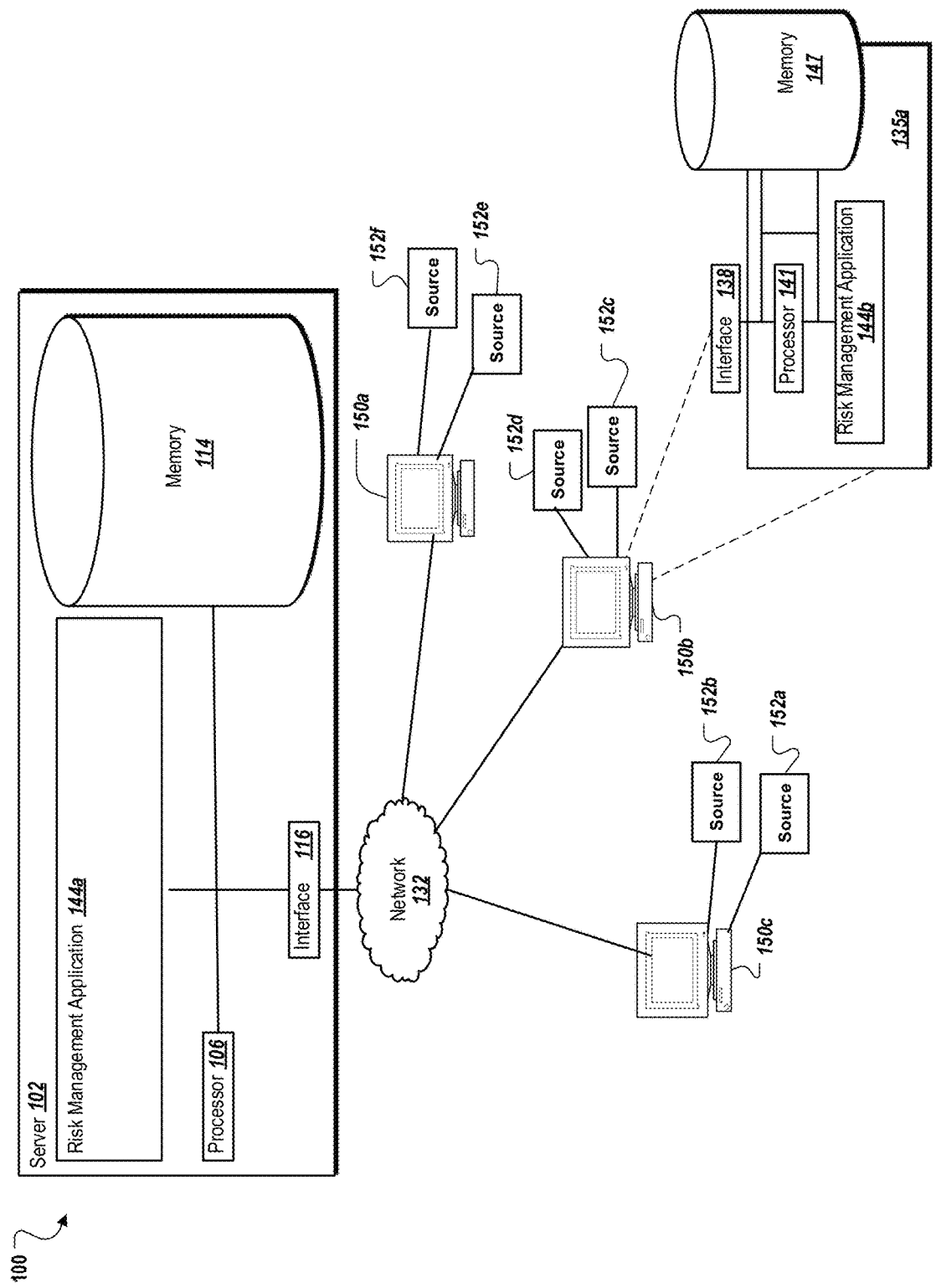
FIGS. 1 and 2 are block diagrams of example flight risk management framework systems in accordance with example implementations.

Turning to the example implementation of FIG. 1, the illustrated system 100 includes or is communicably coupled with a server 102 and one or more computing devices 150, at least some of which communicate across network 132. In general, the system 100 depicts an example configuration of a system capable of providing a flight risk management framework via the server 102 and computing devices 150.

In general, the server 102 stores one or more applications, such as the risk management application 144a. The risk management application 144a can be executed as software or hardware. In some instances, the server 102 stores a plurality of applications in addition to the risk management application 144a, while in other instances, the server 102 can be a dedicated server meant to store and execute only the risk management application 144a.

At a high level, the server 102 comprises an electronic computing device operable to receive, transmit, process, store, or manage data and information associated with the system 100. As used in the present disclosure, the term "computer" or "computing device" is intended to encompass any suitable processing device. For example, although FIG. 1 illustrates a single server 102, system 100 can be implemented using two or more servers 102, as well as computers other than servers, including a server pool. Indeed, server 102 can be any computer or processing device such as, for example, a blade server, general-purpose personal computer (PC), Macintosh, workstation, UNIX-based workstation, or any other suitable device. In other words, the present disclosure contemplates computers other than general-purpose computers, as well as computers without conventional operating systems. Further, illustrated server 102 can be adapted to execute any operating system, including Linux, UNIX, Windows, Mac OS, or any other suitable operating system. According to one embodiment, server 102 also includes or is communicably coupled with an air traffic control system or a flight management system.

In some implementations, and as shown in FIG. 1, the server 102 includes a processor 106, an interface 116, a memory 114, and framework application 104. The interface 116 is used by the server 102 for communicating with other systems in a client-server or other distributed environment (including within system 100) connected to the network 132. Generally, the interface 116 comprises logic encoded in software and/or hardware in a suitable combination and operable to communicate with the network 132. More specifically, the interface 116 can comprise software supporting one or more communication protocols associated with communications such that the network 132 or interface's hardware is operable to communicate physical signals within and outside of the illustrated system 100.

Generally, the network 132 facilitates wireless or wireline communications between the components of the system 100 (i.e., between the server 102 and the computing devices 150), as well as with any other local or remote computer, such as additional servers, or other devices communicably coupled to network 132 but not illustrated in FIG. 1. The network 132 is illustrated as a single network in FIG. 1, but can be a continuous or discontinuous network without departing from the scope of this disclosure, so long as at least a portion of the network 132 can facilitate communications between senders and recipients.

In still other examples, the network 132 includes a messaging backbone. The network 132 can be all or a portion of an enterprise or secured network, while in another instance at least a portion of the network 132 represents a connection to the Internet. In some instances, a portion of the network 132 is a virtual private network (VPN), such as, for example, the connection between the computing device(s) 150 and the server 102. Further, all or a portion of the network 132 can comprise either a wireline or wireless link. Example wireless links include 802.11a/b/g/n, 802.20, WiMax, and/or any other appropriate wireless link. In other words, the network 132 encompasses any internal or external network, networks, sub-network, or combination thereof operable to facilitate communications between various computing components inside and outside the illustrated system 100.

The network 132 can communicate, for example, Internet Protocol (IP) packets, Frame Relay frames, Asynchronous Transfer Mode (ATM) cells, voice, video, data, and other suitable information between network addresses. The network 132 can also include one or more local area networks (LANs), radio access networks (RANs), metropolitan area networks (MANs), wide area networks (WANs), all or a portion of the Internet, and/or any other communication system or systems at one or more locations.

As illustrated in FIG. 1, server 102 includes a processor 106. Although illustrated as a single processor 106 in FIG. 1, two or more processors can be used according to particular needs, desires, or particular embodiments of system 100. Each processor 106 can be a central processing unit (CPU), a blade, an application specific integrated circuit (ASIC), a field-programmable gate array (FPGA), or another suitable component. Generally, the processor 106 executes instructions and manipulates data to perform the operations of server 102 and, specifically, risk management application 144a. Specifically, the server's processor 106 executes the functionality required to receive and respond to requests from the computing devices 150.

Regardless of the particular implementation, "software" includes computer-readable instructions, firmware, wired or programmed hardware, or any combination thereof on a tangible medium operable when executed to perform at least the processes and operations described herein. Indeed, each software component can be fully or partially written or described in any appropriate computer language including C, C++, Java, Visual Basic, assembler, Perl, any suitable version of 4GL, as well as others. It will be understood that while portions of the software illustrated in FIG. 1 are shown as individual modules that implement the various features and functionality through various objects, methods, or other processes, the software can instead include a number of sub-modules, third party services, components, libraries, and such, as appropriate. Conversely, the features and functionality of various components can be combined into single components as appropriate.

The server 102 also includes memory 114. Memory 114 can include any memory or database module and can take the form of volatile or non-volatile memory including, without limitation, magnetic media, optical media, random access memory (RAM), read-only memory (ROM), removable media, or any other suitable local or remote memory component. Memory 114 can store various objects or data, including classes, frameworks, applications, backup data, business objects, jobs, web pages, web page templates, database tables, repositories storing business and/or dynamic information, and any other appropriate information including any parameters, variables, algorithms, instructions, rules, constraints, or references thereto associated with the purposes of the server 102. Additionally, memory 114 can include any other appropriate data, such as VPN applications, firmware logs and policies, firewall policies, a security or access log, print or other reporting files, as well as others.

Figure 2:
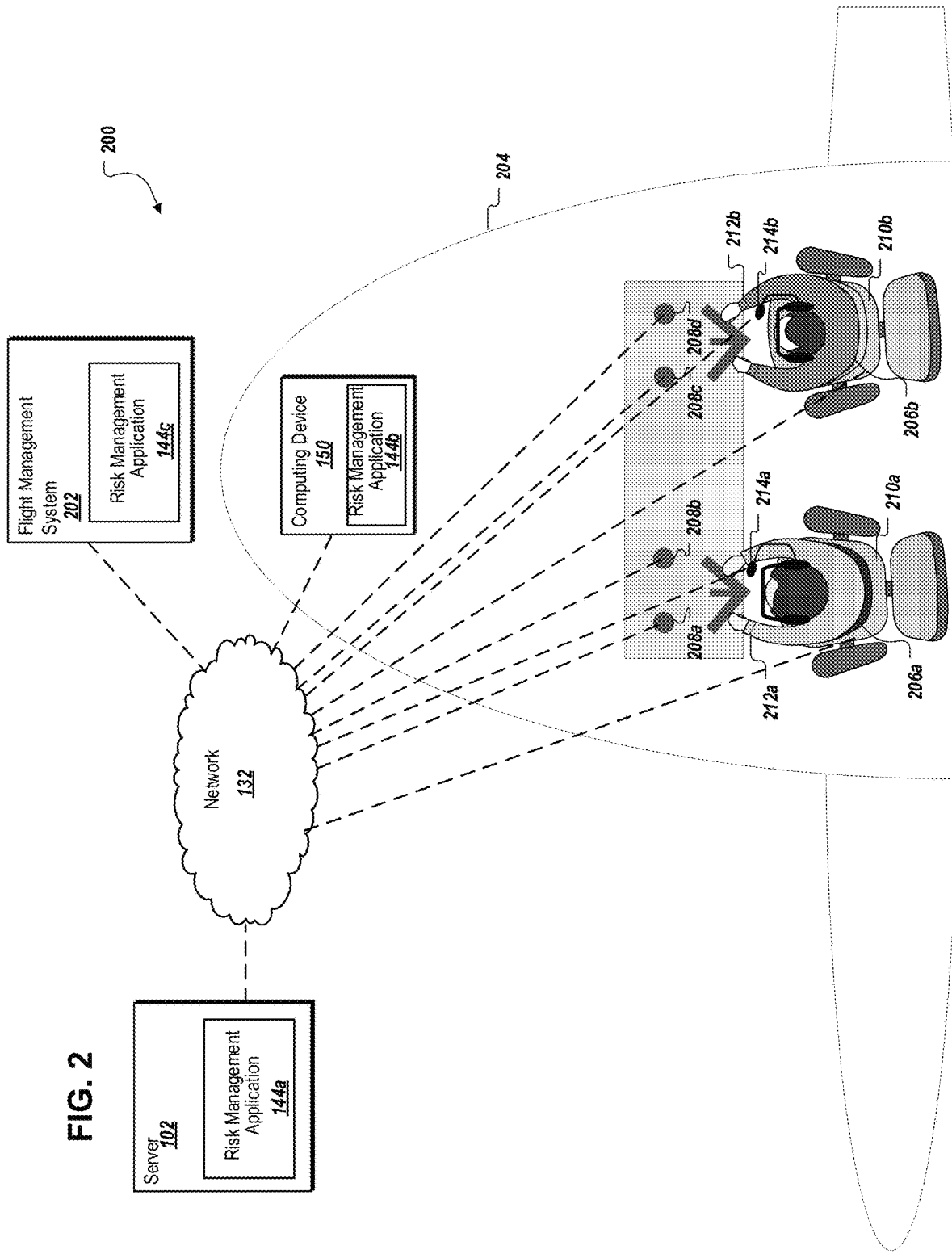

The system 100 can also include one or more computing devices 150 (e.g., in-flight risk mitigation (IRM) computers as shown and described in reference to FIG. 2). Further, computing devices 150 can be additional servers, or hardware or software modules incorporated into server 102. Computing devices 150, generally, include a risk management application 144b or computer code and/or routines defining risk management methods. In some implementations, computing devices 150 include a processor 141, an interface 138, a risk management application 144b, and memory 147. It will be understood that there can be any number of computing devices 150 associated with, or external to, system 100. For example, while illustrated system 100 includes three computing devices (150a, 150b, and 150c), alternative implementations of system 100 can include multiple computing devices 150 communicably coupled to the server 102, or any other number suitable to the purposes of the system 100.

Each computing device 150 can include an input device, such as a keypad, touch screen, mouse, or other device that can accept user information, and an output device that conveys information associated with the operation of the server 102 or the computing device 150 itself, including digital data, visual information, and the risk management application 144b. Both the input and output device can include fixed or removable storage media such as a magnetic or solid state storage media or other suitable media to both receive input from and provide output to users of the computing device through a display, such as a user interface. As described above, in many implementations, the computing devices 150 are networked devices or computer systems.

In some implementations, computing device(s) 150 can be located within a vehicle. For example, computing device(s) 150 can be installed on an aircraft. Each computing device 150 can be associated with particular users of the system 100. For example, the computing device 150a can be associated with a flight crew member, such as a pilot, or a flight operations manager. In some implementations, the computing device 150a is associated with a vehicle (e.g., aircraft 204 of FIG. 2). It will also be understood that the system 100 can include a variety of computing devices 150 not illustrated in FIG. 1, such as administrator or network support systems.

Further, each computing device 150 can include a graphical user interface (GUI) 138 comprising a graphical user interface operable to interface with at least a portion of system 100 for any suitable purpose, including generating a visual representation of the risk management application 144b (in some instances) and the interactions with the network 132, including the responses received from the server 102 received in response to the requests sent by the computing device(s) 150. Generally, through the GUI 138, the user is provided with an efficient and user-friendly presentation of data provided by or communicated within the system. The term "graphical user interface," or GUI, can be used in the singular or the plural to describe one or more graphical user interfaces and each of the displays of a particular graphical user interface. Therefore, the GUI 138 can represent any graphical user interface, including but not limited to, a web browser, touch screen, or command line interface (CLI) that processes information in system 100 and efficiently presents the information results to the user.

In general, the GUI 138 can include a plurality of user interface (UI) elements, some or all associated with the risk management application 144b, such as interactive fields, pull-down lists, and buttons operable by the user of computing device(s) 150. These and other UI elements can be related to or represent the functions of the risk management application 144b, as well as other software applications executing at the computing device(s) 150.

Each computing device is communicably coupled to one or more sources 152 of fatigue indicator data and is configured to receive and evaluate the fatigue indicator data. For example, computing device 150a can receive fatigue indicator data from one or more sources 152e, 152f of fatigue indicator data for a first flight crew member on a first aircraft, computing device 150b can receive fatigue indicator data from one or more sources 152c, 152d of fatigue indicator data for a second flight crew member on a second aircraft, and computing device 150c can receive fatigue indicator data from one or more sources 152a, 152b of fatigue indicator data for a third flight crew member on a third aircraft. Fatigue indicator sources can include client devices, and/or electronic sensors. The sources 152 can also be "smart" or Internet-enabled devices. For example, the sources 152 can be measurement devices or sensors capable of independent and automatic communication over one or more networks. For example, the sources 152 can be any suitable source of data related to a measured fatigue indicator including, but not limited to, eye tracking sensors, accelerometers, audio sensors, microphones, human physiology sensors, verbal command protocol transcripts, sleep wake history, flight schedules, personnel schedules, personnel training databases, command protocol databases, and personnel biological monitoring servers or devices. Furthermore, each computing device 150 can communicate with fatigue indicator sources 152 directly (e.g., through a wired or wireless communication channel) or via the network 132. In some implementations, the server 102 receives data from the fatigue indicator sources 152 over the network 132. The server 102 can process the data, for example, using a risk management application 144a stored at and executed by the server 102.

While FIG. 1 is described as containing or being associated with a plurality of elements, not all elements illustrated within system 100 of FIG. 1 can be utilized in each alternative implementation of the present disclosure. Additionally, one or more of the elements described herein can be located external to system 100, while in other instances, certain elements can be included within or as a portion of one or more of the other described elements, as well as other elements not described in the illustrated implementation. Further, certain elements illustrated in FIG. 1 can be combined with other components, as well as used for alternative or additional purposes in addition to those purposes described herein.

FIG. 2 depicts an exemplary in-flight risk management (IRM) system 200 for managing flight risk. The IRM system 200 includes or is communicably coupled with a server 102, a flight management system 202, and one or more IRM computers 150, at least some of which communicate across network 132. In general, the IRM system 200 depicts an example configuration of a system capable of providing a flight risk management framework via the server 102, flight management system 202, and computing device(s) 150. As depicted in FIG. 2, the computing device(s) 150 include a risk management application 144b. In some implementations, the server 102 also includes a processor (e.g., processor 106 of FIG. 1), an interface (e.g., interface 116 of FIG. 1), and a memory (e.g. memory 114 of FIG. 1). Server 102 is communicably coupled to the flight management system 202 and computing device(s) 150. For example, server 102 can provide information to the computing device(s) 150 over the network 132. Server 102 can also receive information from flight management system 202, the computing device(s) 150, and a plurality of sensors onboard the aircraft 204 over network 132.

In some implementations, flight management system 202 includes a server device and a memory device. For example, flight management system 202 can include a server coupled to a memory device that stores one or more applications, such flight risk management application 144c. In some implementations, flight management system 202 stores flight information for a plurality of flights. For example, flight management system 202 can store information that includes, but is not limited to, flight identification numbers, scheduled flight departure times, estimated flight arrival times, the identity of crew members scheduled to be on each flight, schedules for each aircraft, flight paths, departure airports, arrival airports, weather data, personnel schedules, personnel training databases, the expected level of familiarity the scheduled crew members have with the aircraft, standard protocol command databases, and a level of threat of each potential risk marker, such as adverse weather conditions, poses.

In some implementations, flight management system 202 is communicably coupled to server 102 and one or more IRM computing devices 150. For example, flight management system 202 can provide information stored on the flight management system 202 to the IRM computing device(s) 150 or the server 102 over the network 132. In some implementations, the flight management system 202 receives information from the server 102 or the IRM computing device(s) 150 for execution by the risk management application 144c stored on the flight management system 202.

Exemplary IRM system 200 further includes a plurality of sensors for monitoring fatigue indicators of one or more users 206a, 206b. In some implementations, the one or more users 206a, 206b are flight crew members of an aircraft 204. For example, the one or more users 206a, 206b can be the pilots of an aircraft 204. In some implementations, the sensors of IRM system 200 are installed within the cockpit of an aircraft 204. In some implementations, the sensors of IRM system 200 can be moved between aircrafts. In some implementations, one or more of the sensors of the IRM system 200 are located outside the aircraft 204. The aircraft 204 of exemplary IRM system 200 can include, but is not limited to, a private airplane, a commercial airplane, or a helicopter.

The plurality of sensors in exemplary IRM system 200 can include, but is not limited to, eye tracking sensors 208, leg movement sensors 210, human physiology sensors 212, and audio sensors 214. In some implementations, the sensors are communicably coupled to the IRM computing device 150 to provide fatigue indicator data associated with one or more users 206 to the IRM computing device 150. In some implementations, the sensors provide fatigue indicator data to the IRM computing device 150 over the network 132. In some implementations, the server 102 receives fatigue indicator data from the sensors over the network 132.

In some implementations, IRM system 200 includes one or more eye tracking sensors 208a, 208, 208c, 208d (referred to generically as eye tracking sensors 208). In some implementations, the eye tracking sensors 208 provide data to the IRM system 200 about the eye movement of user 206a and user 206b (referred to collectively as users 206 or generically as user 206). For example, eye tracking sensors 208 can determine the number of eyelid closures (i.e. blinks) that a flight crew member experiences in a minute. In some examples, the eye tracking sensors 208 can determine the length of time that a user's 206 eyelids are closed. In some examples, the eye tracking sensors 208 monitor the eye movement of a pilot (e.g., one of users 206) to determine whether the pilot's gaze is fixed on a particular point, and determine the length of time the pilot is fixed on that point. In some examples, the eye tracking sensors 208 determine whether a pilot is scanning the field of vision. In some implementations, the eye tracking sensors 208 track the eye movement of multiple users 206. For example, the eye tracking sensors can track the eye movements of a pilot of the aircraft 204 (e.g., one of users 206) and the eye movement of a co-pilot of the aircraft 204 (e.g., one of users 206). Data provided by the eye tracking sensors 208 to the IRM system 200, such as prolonged gazes, increased blink rate, or a combination thereof, can provide an indication of an increasing fatigue level of the respective flight crew member.

In some implementations, the eye tracking sensors 208 are provided as infrared sensors. In some implementations, the eye tracking sensors 208 are provided as visible light, infrared-free tracking sensors. In some implementations, the eye tracking sensors 208 are incorporated into a control panel of the aircraft 204. In some implementations, the eye tracking sensors 208 are detachably fixed to the aircraft 204, and can be moved between aircrafts. In some implementations, the eye tracking sensors 208 are communicably coupled to the IRM computing device 150 to provide eye tracking data to the computing device 150 to be processed by risk management application 144b stored on the IRM computing device 150. In some implementations, the eye tracking sensors 208 are communicably coupled to the server 102 to provide eye tracking data to the server 102 to be processed by risk management application 144a stored on the server 102.

In some implementations, IRM system 200 includes one or more leg movement sensors 210a, 210b (referred to generically as leg movement sensors 210). In some examples, each leg movement sensor 210 detects the movement of a respective flight crew member's (e.g. users 206a, 206b) legs in his seat. In some examples, the leg movement sensors 210 detect changes in the pressure provided by a flight crew member's legs on his seat. In some implementations, the leg movement sensors 210 detect periodic leg movement. In some implementations, multiple leg movement sensors 210 can be provided to monitor the leg movement of multiple flight crew members, such as pilot and a co-pilot of the aircraft 204 (e.g., users 206a, 206b). Data provided by the leg movement sensors 210 to the IRM system 200, such as a decreased rate in changes in pressure provided by a pilot's legs on his seat, can provide an indication of an increasing fatigue level of a pilot.

In some implementations, the leg movement sensors 210 can be incorporated into the seat cushion of a flight crew member's chair in the aircraft 204. In some examples, leg movement sensors 210 can be provided as a detachable cushions or pads that can be placed on the one or more flight crew members' seats. In some implementations, the leg movement sensors 210 can be provided as one or more pressure sensors. In some implementations, the leg movement sensors 210 can be provided as one or more accelerometers. In some implementations, the leg movement sensors 210 can be provided as one or more semiconductor sensors. In some implementations, the leg movement sensors 210 are communicably coupled to IRM computing device 150 to provide leg movement data to the IRM computing device 150 to be interpreted and processed by risk management application 144b stored on the IRM computing device 150. In some implementations, the leg movement sensors 210 are communicably coupled to the server 102 to provide leg movement data to the server 102 to be processed by risk management application 144a stored on the server 102.

In some implementations, IRM system 200 includes one or more human physiology sensors 212a, 212b (referred generically as human physiology sensors 212). In some examples, human physiology sensors 212 can be used to monitor a plurality of human physiology indicators for one or more flight crew members (e.g., users 206a, 206b). In some examples, human physiological indicators monitored by the human physiology sensors 212 include, but are not limited to, pulse, blood pressure, rate of breathing, temperature, sleep wake patterns, heart rate variability (HRV), galvanic skin response (GSR), skin temperature, electroencephalogram (EEG) outputs, electrocardiogram (EKG) outputs, and other like physiological indicators. Data provided by human physiology sensors 212, such as a decreasing heart rate can provide an indication of an increased fatigue level of a pilot. In some implementations, chemical measurements can be conducted on blood, sweat, saliva, and urine of the flight crew members to monitor physiological indicators of the flight crew members.

In some implementations, the one or more human physiology sensors 212 can be provided as wearable devices, such as actiwatches, that can be worn by one or more pilots (e.g., users 206a, users 206b). In some implementations, the human physiology sensors 212 can be provided as a device that can be worn of the wrist of a user 206. In some implementations, the human physiology sensors 212 can be imbedded into a jacket that can be worn by the user 206. In some implementations, the human physiology sensors 212 can be provided as semiconductor sensors. In some implementations, the human physiology sensors 212 are located within the cockpit of an aircraft 204. In some implementations, the human physiology sensors 212 are moveable between aircrafts. In some implementations, one or more of the physiology sensors 212 are located outside the aircraft 204. For example, one or more of the physiology sensors 212 can be used to monitor human physiology indicators of a remote operator of the aircraft 204 located at an on-ground control location. In some implementations, the human physiology sensors 212 are communicably coupled to IRM computing device 150 to provide human physiological data to the IRM computing device 150 to be processed by risk management application 144b stored on the IRM computing device 150. In some implementations, the human physiology sensors 212 are communicably coupled to the server 102 to provide human physiological data to the server 102 to be processed by risk management application 144a stored on the server 102.

In some implementations, IRM system 200 includes one or more audio sensors 214a, 214b (referred generically as human audio sensors 214). In some implementations, the audio sensors 214 can be configured to record and monitor the speech of one or more flight crew members (e.g., users 206a, 206b). In some examples, the audio sensors 214 capture audio data including, but not limited to, the spoken words, tone, and other like verbal cues of the one or more flight crew members. In some implementations, the audio sensors 214 can be incorporated into the control panel of the aircraft 204. In some implementations, the audio sensors 214 can be provided as one or more microphones. In some implementations, the audio sensors 214 are located within the cockpit of an aircraft 204. Data provided by audio sensors 214 to the IRM system 200, such as errors in standard protocol commands, and changes in tone, can indicate an increasing fatigue level of a pilot. In some implementations, the audio sensors 214 can be communicably coupled to IRM computing device 150 to provide audio data to the IRM computing device 150 to be processed by risk management application 144b stored on the IRM computing device 150. In some implementations, the audio data provided by the audio sensors 214 to a IRM computing device 150 can be processed using a trained machine learning model of the IRM computing device 150. In some implementations, the audio sensors 214 are communicably coupled to the server 102 to provide audio data to the server 102 to be processed by risk management application 144a stored on the server 102.

In some implementations, the audio data collected by the audio sensors 214 is provided to a machine learning model that is trained to detect and analyze standard protocol command litanies that are conducted for various portions of the flight. For example, in some implementations, the audio sensors 214 continuously collect the speech of the flight crew members during a flight and transmit the recorded speech to a trained machine learning module in real time. The trained machine learning module analyzes the audio data collected by the audio sensors 214 in real time and detects if a standard protocol command has been spoken by one of the flight crew members. For example, the machine learning module can monitor for trigger word(s) or actions that indicate the initiation of a standard command litany. Trigger words may be, for example, the expected first word or phrase that begins a command litany. In some implementations, the IRM computer 150 is integrated into a flight control system to monitor for actions that are associated with standard commands (e.g., as listed in Table 1 below). Upon detecting the action the IRM computer 150 can trigger the machine learning module to begin analyzing for a proper and timely command/response sequence. In some implementations, to avoid integration with the flight control systems, cockpit cameras can be employed along with machine vision algorithms to monitor for and detect actions associated with command litanies.

In response to detecting that a standard protocol command litany has been initiated, the trained machine learning module analyzes, in real time, the subsequent audio data collected by the audio sensors 214 to determine whether the appropriate response(s) to the initial command have been provided by the flight crew members. In some implementations, if it is detected, based on real time analysis of the audio data, that a flight crew member delays in providing or fails to provide the appropriate response to the detected command, this can be indicative that the flight crew member is experiencing increased fatigue. In some implementations, the machine learning module analyzing the data provided by the audio sensors 214 is trained to differentiate between standard protocol commands and other conversations between the flight crew members. As such, the trained machine learning model can be used to detect and analyze whether a flight crew members accurately performs a standard protocol command litany. In some implementations, the IRM computing devices can be triggered to begin listening for a command litany based a pre-defined action associated with the command litany. Table 1 below provides examples of standard protocol commands and, in some cases, actions associated with a command litany.

| ACTION | PILOT FLYING CALL/RESPONSE | PILOT NOT FLYING CALL/RESPONSE |
|---|---|---|
| START BUTTON DEPRESS | "TIME" | "TIME" "HYD PRESSURE UP, PUMP LIGHT OUT, OIL PRESS LIGHT OUT, FUEL PRESS LIGHT OUT" |

-continued

| ACTION | PILOT FLYING CALL/RESPONSE | PILOT NOT FLYING CALL/RESPONSE |
|---|---|---|
| STARTING ENGINE STABILIZED | "NG AND $T_5$ STABILIZED, STARTER DISENGAGED, BLEED (ENG #) TO HIGH" "CLEAR (ENG #)" | "BLEED (ENG #) TO HIGH CLEAR (ENG #)" |
| POWER LEVER ADVANCE FOR TAKEOFF | "SET POWER" | "SPOILERS RETRACTED, AUTOFEATHER ARMED, POWER SET" |
| 50 KIAS (INDICATORS AND SYSTEMS NORMAL) | | "50 KNOTS" |
| AIRSPEED AT $V_1$ | | "$V_1$, ROTATE" |
| POSITIVE RATE OF CLIMB | "GEAR UP, BLEEDS 1 AND 4 LOW" | "POSITIVE RATE" "GEAR SELECTED UP, BLEEDS 1 AND 4 LOW" |
| 400' AGL | "ACCELERATING" | "400 FEET, LOOKING FOR (FLAP RETRACTION AIRSPEED)" |
| FLAP RETRACTION AIRSPEED ($V_2$ FOR FLAPS ZERO) | "AIRSPEED (STATE SPEED) SELECT FLAPS ZERO" | "FLAPS SELECTED ZERO" |
| THIRD SEGMENT CLIMB | "AUTOFEATHER OFF, SET CLIMB POWER, AFTER TAKEOFF CHECK" "MY POWER" | "YOUR POWER" (AFTER DESLECTING AUTOFEATHER AND SETTING POWER) "AFTER TAKEOFF CHECK COMPLETE" (AFTER COMPETING CL) |
| AIRSPEED DEVIATES +5/−0 KIAS FROM $V_2$ OR $V_2$ + 10 SPEED | "INCREASING/DECREASING AIRSPEED" | "AIRSPEED___KNOTS SLOW/FAST" |
| ABNORMAL OR EMERGENCY CONDITION PRIOR TO $V_1$ (IDENTIFIED BY PNF) | "ABORTING" | "ABORT" (STATE PROBLEM) |
| PF ELECTS TO ABORT PRIOR TO $V_1$ | "ABORTING" (STATE PROBLEM, TIME PERMITTING) | "ROGER" |
| ENGINE MALFUNCTION AT OR AFTER $V_1$ (SEQUENCE DEPENDS ON WHERE FAILURE OCCURS) | "GEAR UP" (CLIMB AT $V_2$) "CONFIRMED" | "ENGINE FAILURE ON NUMBER 1, MAX POWER SET, POSITIVE RATE" "GEAR SELECTED UP, PROP DID NOT FEATHER" "NUMBER 1 CONDITION LEVER IDENTIFIED" "FUEL SHUT-OFF" |
| 400' AGL | "ACCELERATING" | "ABOVE 400 FEET, LOOKING FOR (AIRSPEED)" |
| FLAP RETRACTION AIRSPEED | "AIRSPEED (STATE SPEED) SELECT FLAPS ZERO" | "FLAPS SELECTED ZERO" |
| THIRD SEGMENT CLIMB | "CONTINUE THE EMERGENCY PROCEDURE" "CONFIRMED" "ROGER" "CONFIRMED" "COMPLETE THE EMERGENCY PROCEDURE CHECKLIST" | "NUMBER 1 POWER LEVER IDENTIFIED" "FLIGHT IDLE, NUMBER 1 CONDITION LEVER IS AT FUEL SHUT-OFF" "NUMBER 1 PULL FUEL OFF HANDLE IDENTIFIED" "PULLED, NO INDICATION OF FIRE" |
| TRANSITION ALTITUDE | "29.92" SET LEFT | "29.92" SET RIGHT |
| AT CRUISE SPEED | "SET CRUISE POWER, CRUISE CHECK" "MY POWER" | "YOUR POWER" (AFTER SETTING POWER) "CRUISE CHECK COMPLETE (AFTER COMPLETING CL)" |
| 10,000 OR BELOW | "DESCENT ARRIVAL CHECK" | "DESCENT ARRIVAL CHECK COMPLETE" (AFTER COMPLETING CL) |
| NEW ASSIGNED ALTITUDE | | (ALTITUDE) SET AND ARMED |
| CLIMB OR DESCENT | "CLIMBING/DESCENDING TO (ASSIGNED ALTITUDE)" | "ROGER", (REPORT ALTITUDE CHANGE TO ATC) |
| WITHIN 1000 FEET OF ASSIGNED ALTITUDE | "PASSING (ALTITUDE) FOR (ASSIGNED ALTITUDE)" | "1000 TO GO" |
| INITIAL COURSE/LOCALIZER MOVEMENT | "COURSE/LOCALIZER ALIVE" | "ROGER" |

-continued

| ACTION | PILOT FLYING CALL/RESPONSE | PILOT NOT FLYING CALL/RESPONSE |
|---|---|---|
| COURSE/LOCALIZER CAPTURE | "COURSE/LOCALIZER CAPTURED" | "ROGER" |
| INITIAL GLIDESLOPE MOVEMENT (PRECISION APPROACH) | "GLIDESLOPE ALIVE" | "ROGER" |
| GLIDESLOPE CAPTURE (PRECISION APPROACH) | "GLIDESLOPE CAPTURED" | "ROGER" |
| APPROACHING THE FAF | "AIRSPEED BELOW 147, SELECT FLAPS 15, SELECT GEAR DOWN, BEFORE LANDING CHECK" | "FLAPS SELECTED 15, GEAR SELECTED DOWN", "BEFORE LANDING CHECK COMPLETE" (AFTER COMPLETING CL) |
| PRIOR TO THE FAF (STABILIZED APPROACH) | "AIRSPEED BELOW 124, SELECT FLAPS 25" "CONDITION LEVER MAX RPM, LANDING CHECK" | "FLAPS SELECTED 25" "GEAR RECHECKED DOWN, FLAPS ARE 25, CONDITION LEVERS MAX RPM, LANDING CHECK COMPLETE" |
| FAF (NON-PRECISION APPROACH) | "TIME" | "TIME STARTED" |
| 100' PRIOR TO DH/MDA | "ROGER, CONTINUING" | "100 FEET ABOVE DH/MDA" |
| DH, RWY ENVIRONMENT INSIGHT | "CONTINUING" (OR OTHER INTENTIONS) | "DH, APPROACH LIGHTS (OR OTHER FEATURES IDENTIFIABLE WITH RWY ENVIRONMENT) IN SIGHT" (POSITION) |
| RWY IN SIGHT | "RWY INSIGHT, LANDING" | "RWY IN SIGHT" (POSITION) |
| DH, RWY ENVIRONMENT NOT IN SIGHT | "MISSED APPROACH" | "MISSED APPROACH" |
| MDA | "CONTINUING" | "MINIMUMS" (STATE TIME/DISTANCE TO GO) |
| RWY ENVIRONMENT INSIGHT | "CONTINUING" (OR OTHER INTENTIONS) | "APPROACH LIGHTS (OR OTHER FEATURES IDENTIFIABLE WITH RWY ENVIRONMENT) IN SIGHT" (POSITION) |
| RWY INSIGHT | "RWY INSIGHT, LANDING" | "RWY IN SIGHT (POSITION)" |
| RWY ENVIRONMENT NOT IN SIGHT AT MAP | "MISSED APPROACH" | "MISSED APPROACH" |
| ±ONE DOT OFF GLIDESLOPE | "CORRECTING (UP/DOWN)" | "ONE DOT (HIGH/LOW) AND INCREASING/DECREASING" |
| ±ONE DOT OFF LOCALIZER/VOR | "CORRECTING (LEFT/RIGHT)" | "ONE DOT (LEFT/RIGHT) AND INCREASING/DECREASING" |
| ±5° ON NDB APPROACH | "CORRECTING (LEFT/RIGHT)" | "___°(LEFT/RIGHT) AND INCREASING/DECREASING" |
| ±10° KNOTS FROM APPROACH SPEED | "INCREASING/DECREASING AIRSPEED" | "AIRSPEED___KNOTS SLOW/FAST" |
| Vref +10/−0 KNOTS | "INCREASING/DECREASING AIRSPEED" | "Vref + ___KNOTS" |
| RATE OF DESCENT EXCEEDS 1000 FEET PER MINUTE | "REDUCING SINK RATE" | "SINK RATE (AMOUNT) INCREASING/HOLDING" |
| GO-AROUND (FLAPS 45°) | (PUSH POWER LEVERS UP, ROTATE TO 8°-12° PITCH ATTITUDE) "SET MAXIMUM POWER, FLAPS 25" | "MAXIMUM POWER SET, FLAPS SELECTED 25" |
| DESCENT STOPPED | "GEAR UP" | "POSITIVE RATE" "GEAR SELECTED UP, LOOKING FOR (FLAPS 15 V$_2$ AIRSPEED)" |
| FLAP RETRACTION AIRSPEED (25° TO 15°) ABOVE 400 FEET AGL | "AIRSPEED (STATE SPEED) SELECT FLAPS 15" "ACCELERATING" | "FLAPS SELECTED 15, CLIMB AT (V$_2$ + 10 AIRSPEED)" "ABOVE 400 FEET, LOOKING FOR (AIRSPEED)" |
| FLAP RETRACTION AIRSPEED (15° TO ZERO) | "AIRSPEED (STATE SPEED) SELECT FLAPS ZERO" "GO-AROUND CHECKLIST" | "FLAPS SELECTED ZERO" |
| BANK ANGLE EXCEEDS 30° | "CORRECTING" | "BANK ANGLE" |
| AIRSPEED DEVIATES ± 10 KIAS | "INCREASING/DECREASING AIRSPEED" | "AIRSPEED___KNOTS SLOW/FAST" |
| ALTITUDE DEVIATES ± 100 FEET | "INCREASING/DECREASING ALTITUDE" | "ALTITUDE___FEET LOW/HIGH" |
| HEADING DEVIATES ± 10° | "CORRECTING LEFT/RIGHT" | "HEADING___° LEFT/RIGHT" |

| ACTION | PILOT FLYING CALL/RESPONSE | PILOT NOT FLYING CALL/RESPONSE |
| --- | --- | --- |
| AIRSPEED DECELERATING THROUGH 40 KIAS | "LOCK THE CONTROLS" | "40 KNOTS" "CONTROLS ARE LOCKED" (AFTER TAKING CONTROL OF THE YOKE AND ENGAGING THE CONTROL LOCK) |
| CROSSWIND LANDING RIGHT SEAT PILOT TAXIING THE AIRCRAFT | "YOUR YOKE, MY TILLER" "NOSE WHEEL STEERING OFF" | "I HAVE THE YOKE" "NOSE WHEEL STEERING OFF" |

While FIG. 2 is described as containing or being associated with a plurality of elements, not all elements illustrated within IRM system 200 of FIG. 2 are utilized in each alternative implementation of the present disclosure. Additionally, one or more of the elements described herein can be located external to IRM system 200, while in other instances, certain elements can be included within or as a portion of one or more of the other described elements, as well as other elements not described in the illustrated implementation. Further, certain elements illustrated in FIG. 2 can be combined with other components, as well as used for alternative or additional purposes in addition to those purposes described herein.

Figure 3A:
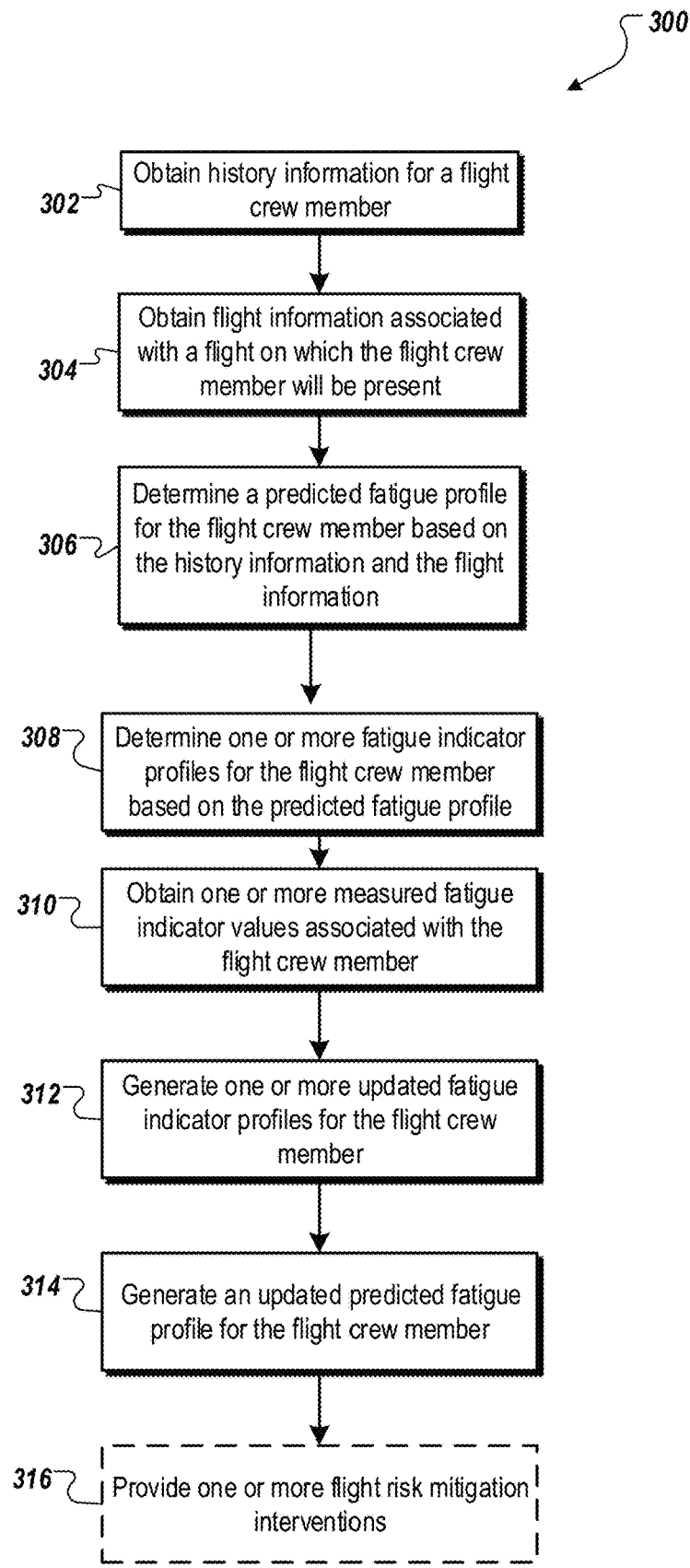
FIG. 3A is a flowchart for an example process for evaluating and reducing flight risk in accordance with an example implementations.

FIG. 3A depicts a flowchart of an example process 300 for evaluating and reducing levels of flight risk due to operator fatigue. In some implementations, the process 300 can be provided as one or more computer-executable programs executed using one or more computing devices (e.g., computing device(s) 150 of FIGS. 1 and 2). In some examples, the process 300 is executed by a system such as IRM system 200 of FIG. 2. In some implementations, all or portions of process 300 can be performed on a remote computing device, a server system (e.g., server 102 of FIG. 2), or a cloud-based server system. For example, all or portions of process 300 can be performed by a computing device that is located within a vehicle (e.g., IRM computing device 150 located on aircraft 204 of FIG. 2).

History information for a flight crew member is obtained (302). For example, IRM computing device 150 obtains history information for a flight crew member 206. In some implementations, the history information is stored locally on IRM computing device 150. In some implementations, history information is obtained from a server (e.g., server 102 of FIG. 2). In some implementations, history information is obtained from a flight management system (e.g., flight management system 202 of FIG. 2). In some implementations, history information is obtained by a server (e.g., server 102 of FIG. 2) from a flight management system (e.g., flight management system 202 of FIG. 2). In some implementations, the history information is obtained from one or more "smart" devices associated with the flight crew member. For example, the history information can be obtained from a "smart" device that is worn by a flight crew member and tracks the sleep and wake activity of the flight crew member. In some implementations, history information can be obtained from other devices that monitor one or more physiological indicators of the flight crew member, such as a blood pressure cuff used to measure pulse and blood pressure. In some implementations, mobile applications stored on a mobile device may be used to detect and track history information of a flight crew member, such as the flight crew member's sleep history.

In some implementations, a computing device (e.g., IRM computing device 150 of FIG. 2) requests history information for the flight crew member from one or more computing devices (e.g., server 102 or flight management system 202 of FIG. 2) and receives the history information for the flight crew member in response to the request (i.e., "pulls" the data). In some implementations, computing devices (e.g., server 102 or flight management system 202 of FIG. 2) send history information to the IRM computing device 150 without having received a request (i.e., "pushes" the data). For example, server 102 can proactively send updates to IRM computing device 150 as the history information of one or more flight crew members changes. For example, server 102 can automatically provide IRM computing device 150 with updated history information for a flight crew member whenever the flight crew member falls asleep or awakens from sleep (e.g., from a rest period during an extended flight), as detected by a smart device worn by the respective flight crew member. In some implementations, history information related to a flight crew member is obtained by IRM computing device 150 at a specified time before the scheduled departure time for a flight that the flight crew member is scheduled to be on. In some implementations, the flight crew member is alerted to submit history information, such as current blood pressure or sleep logs, to the IRM computing device 150 prior to a flight. In some implementations, obtaining history for the flight crew member includes obtaining a profile for the flight crew member.

The history information can include, but is not limited to, the rest and wake activity of a flight crew member for a specified period of time. For example, history information can include the rest and wake activity of a flight crew member for the last 24 to 72 hours. Sleep loss is associated with decreased capacity to perform cognitive tasks and increased variability in performance, leading to greater possibility of errors, incidents, and accidents. As such, the rest and wake activity of a flight crew member may be an important factor to evaluate in predicting fatigue for the flight crew member.

In some implementations, the rest and wake activity for a flight crew member is determined based on the flight history of the flight crew member for specified a period of time. For example, based on the flight crew member's flight history for a period of time, the sleep received by the flight crew member during the period of time (i.e., the pilot's sleep history) can be determined. For example, a fatigue model described in "A Predictive Model of Work-Related Fatigue Based on Hours of Work", Journal of Occupational Health and Safety, vol. 13, 471-485 (1997) correlates an on-duty/off-duty schedule of a user with the amount of sleep the user has received. This model positively correlates "on-duty" time with being awake to determine the predicted amount of sleep received by the user. In addition, this model accounts for time of day, including time shifting events, such as changing time zones, and jet lag. Other biomathematical models for predicting fatigue may also be used to generate a predicted sleep history for a flight crew member based on the flight crew member's flight history. In some implementations, if a flight that the flight crew member is scheduled to work exceeds a threshold length (e.g., overseas or international flights), a short rest or sleep may be predicted for the flight crew member during the flight.

In some implementations, the rest and wake activity for a flight crew member is determined based on exponential and power law models. Using these models, a sleep regulating variable (S) decreases as an exponential function when the flight crew member is sleeping and increases as a power law function when the flight crew member is awake. This model also accounts for several factors that can be identified from a flight crew member's work schedule that affect sleep estimations. These factors predictive of fatigue include, but are not limited to, the start time of a flight the flight crew member has recently worked on, the length of a flight that the flight crew member has recently worked on, the length of time the flight crew member has been away from home, the local arrival time of a flight the flight crew member has recently worked on, commute and transit times experienced by the flight crew member between flights, the start time of the next flight the flight crew member is scheduled to work, the length of the next flight the flight crew member is scheduled to work, the number and length of opportunities that the flight crew member had to sleep between flights, the total number of flights that the flight crew member is scheduled to work during a predetermined time period, the change in time zones experienced by the flight crew member over a predetermined period, and the total amount of time between flights on which the flight crew member is scheduled to work. The correlation between fatigue levels and each of the above-recited factor can be measured using a variety of methods, such as using subjective scales, wearable devices (such as actiwatches), polysomnography tests, and psychomotor vigilance tests (PVT).

Figure 5:
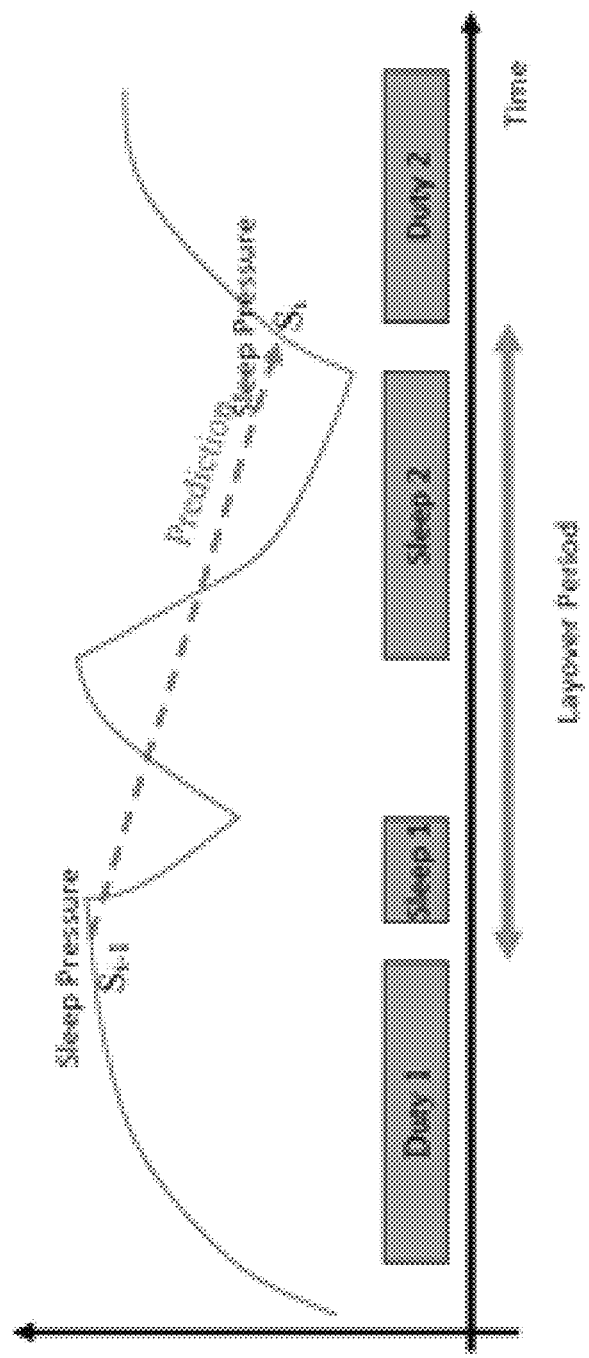
FIG. 5 is a diagram of an example fatigue profile generated by a flight risk management application in accordance with example implementations.

In addition, this model can account for environmental factor that influence sleep, such as global economic factors, geo political factors, weather, and global events. FIG. 5 depicts an example predicted fatigue profile generated for a flight crew member using the above-described exponential and power law models, with levels of fatigue (or sleep pressure) increasing along the y-axis.

These factors determined from the flight crew member's schedule and other relevant factors can be processed by a trained machine learning model to predict the sleep of the flight crew member, which can then be used to predict fatigue for the flight crew member, using the above-described exponential and power law models in conjunction with historical data to generate a predicted fatigue profile for the flight crew member.

In some implementations, the trained machine learning model utilizes a recursive feature elimination algorithm to predict fatigue for a flight crew member based on the flight crew member's work schedule and other relevant factors. In some implementations, clustering methods are used to analyze fatigue prediction data and improve the machine learning model used to predict fatigue based on history information, such as a flight crew member's work schedule. The history information can also include training history of the flight crew member. In some implementations, history information includes the flight schedule for the flight crew member for a specified number of days prior to the crew member's upcoming flight. For example, the history information can include the flight crew member's rest and wake activity for a period of time (e.g., the prior two days, the prior week, etc.), the flight crew member's training history, and the flight crew member's flight schedule for a period of time (e.g., the previous three days, the previous week, etc.).

In some implementations, the history information includes prior fatigue profile data and measured fatigue indicator values for the flight crew member. For example, the history information can include prior predicted fatigue profiles generated for the flight crew member on previous flights and fatigue indicator values measured for the flight crew member by fatigue indicator sensors on the respective flights. By including the measured fatigue indicators values and the fatigue profile generated for the flight crew member during a recent flight in the information to be analyzed by the machine learning model to generate a predicted fatigue profile, the accuracy of predicted fatigue profile generated for the flight crew member for an upcoming flight can be improved because the measured fatigue indicators values and the previous fatigue profile provide information that is strongly correlated of the current level of fatigue of the flight crew member.

Figure 7:
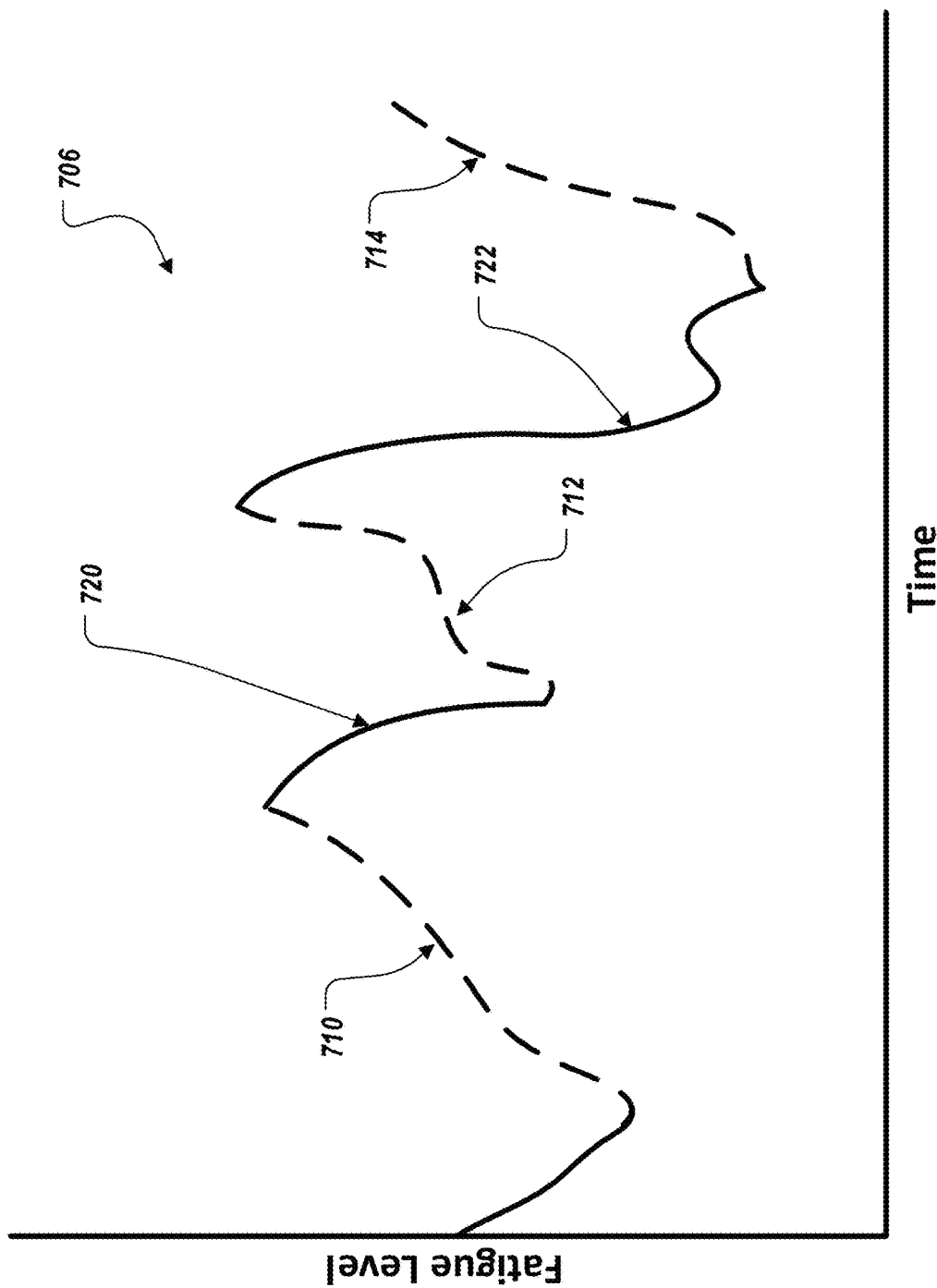
FIG. 7 is an example fatigue profile generated by a flight risk management application in accordance with example implementations.

In some implementations, the history information can include the measured fatigue indicator values and the fatigue profiles generated for the flight crew member over several flights worked by the flight crew member over a predetermined period of time (e.g., previous 12 hours, previous 24 hours, etc.). FIG. 7 depicts a fatigue profile for a flight crew member generated over a predetermined period of time (e.g., the previous 24 hour time period) that includes three fatigue profiles 710, 712, 714 generated during three flights worked by the flight crew member during the time period, as well as the predicted fatigue levels 720, 722 of the flight crew member during periods of rest between each of the flights. The fatigue profiles 710, 712, 714 are generated based on fatigue indicator sensor data collected during the respective flights. The accuracy of the predicted fatigue profile generated for the flight crew member for an upcoming flight can be improved, by, for example, including one or more of the fatigue profiles 710, 712, 714 generated during recent flights worked by the flight crew member, as well as the measured fatigue indicator values corresponding to the fatigue profiles 710, 712, 714, in the data analyzed by the machine learning model to generate a predicted fatigue profile.

Flight information associated with an upcoming flight on which the flight crew member will be present is obtained (304). For example, an onboard computing device (e.g., IRM computing device 150 of FIG. 2) can obtain flight information for a flight on which the flight crew member will be present. In some implementations, the flight information can be stored locally on the onboard computing device. In some implementations, flight information is obtained from one or more computing devices (e.g., from flight information system 202). For example, the onboard computing device can request information for the next flight that a specified flight crew member is scheduled to be on from a flight management system, and receive the flight information in response to the request (i.e., "pulls" the data). In some implementations, a flight management system sends flight information to the onboard computing device without having received a request from the computing device (i.e., "pushes" the data). For example, a flight management system can proactively send flight information to an onboard computing device as a flight schedule for the specified flight crew member changes, for instance, whenever the flight crew gets scheduled for a flight or a flight that the flight crew member is scheduled to be on is rescheduled or cancelled.

Flight information includes, but is not limited to, information related to the flight identification number, the scheduled time of departure for the flight, the estimated time of arrival for the flight, the identity of other crew members scheduled to be on the flight, the type of aircraft to be used for the flight, the flight path, the departure airport, the arrival airport, weather data, the expected level of familiarity the scheduled crew members have with the aircraft, and the level of error threat that each potential risk marker expected to be experienced during the flight, such as adverse weather conditions, poses. In some implementations, the flight information further includes Line Operations Safety Assessment (LOSA) data received from the Federal Aviation Administration (FAA), including data related to pilot errors and threats during flight. Flight information can also include data from one or more safety reports from other flights.

Figure 4A:
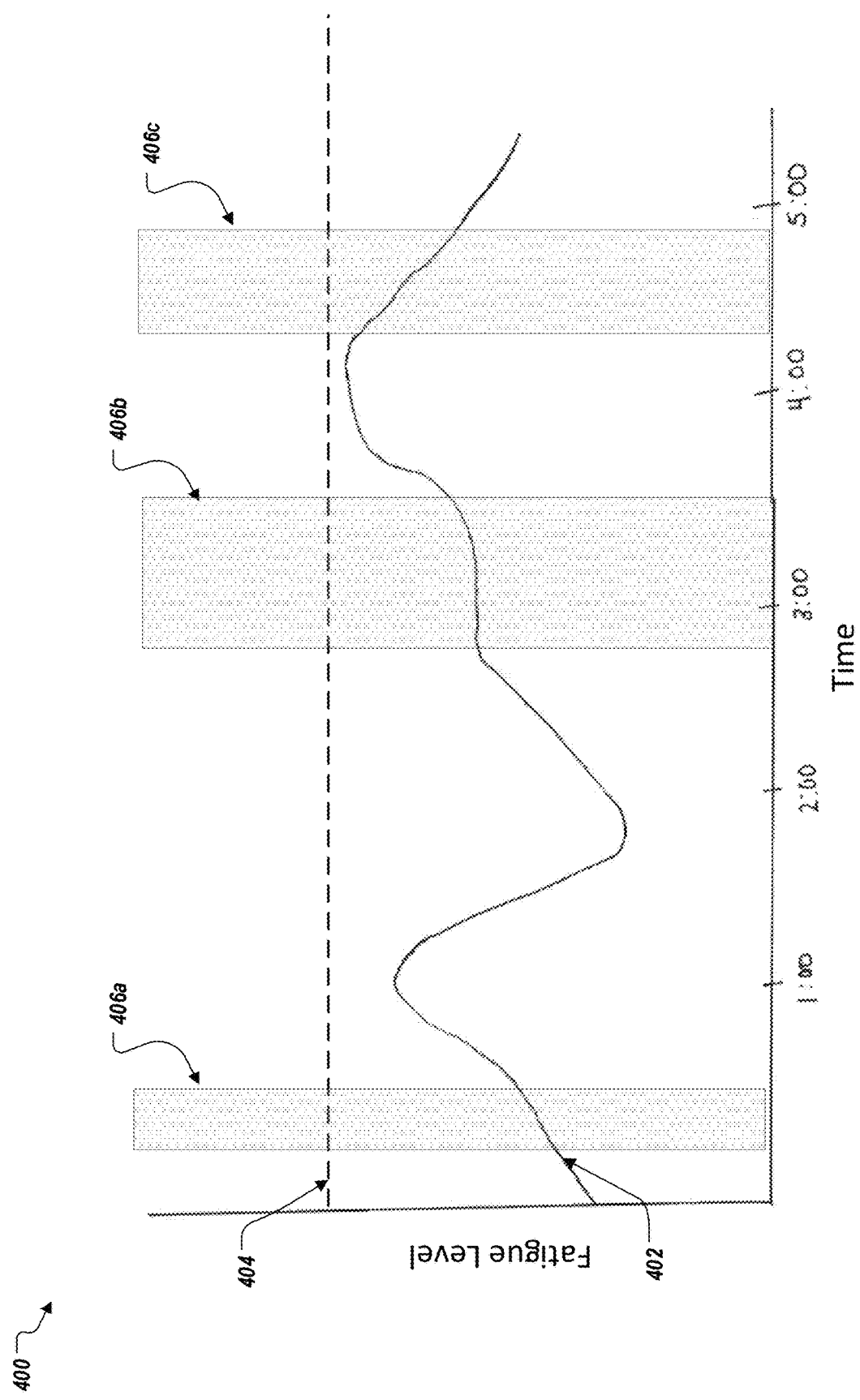
FIGS. 4A-4F are diagrams of example fatigue profiles and/or fatigue indicator profiles generated by a flight risk management application in accordance with example implementations.

A predicted fatigue profile for the flight crew member is determined based on the history information and the flight information (306). In some implementations, the various items of history information data and flight information data are weighted according to their relevance in predicting fatigue. For example, the types of history information and flight information that are more predictive of a flight crew member's fatigue may be weighted more heavily than the types of history information and flight information data that have a weaker correlation with flight crew member fatigue. In some implementations, the predicted fatigued profile is determined by a risk management application (e.g., risk management application 144b of FIG. 2) executed by the onboard computing device (e.g., IRM computing device 150 of FIG. 2). In some implementations, the fatigue profile can be determined by a risk management application (e.g., risk management application 144a of FIG. 2) executed by a server (e.g., server 102 of FIG. 2). An exemplary predicted fatigue profile is depicted in FIG. 4A. As depicted in FIG. 4A, the predicted fatigue profile 400 includes the user's predicted level of fatigue 402 over a period of time. For example, the predicted fatigue profile 400 can represent a pilot's predicted level of fatigue 402 over the duration of a flight, where the duration of the flight is determined based on the flight information received by the computing device.

A plurality of critical event indicators (or risk markers) 406a, 406b, 406c (referred to generically as critical event indicators 406) can be included in the predicted fatigue profile 400. For example, a computing device generating the predicted fatigue profile 400 can identify critical events for the flight based on the flight information received by the IRM computing device 150. Based on the flight information, the computing device can correlate the critical events to times in the predicted fatigue profile 400 when the critical events are likely to occur. For example, the predicted fatigue profile 400 can include critical event indicators 406 for portions of the flight during which a critical event is occurring. Critical events can include, but are not limited to, take-off, landing, expected hazardous weather, changes in airport conditions, and flight through crowded airspace. For example, predicted fatigue profile 400 includes critical event indicators corresponding to takeoff 406a, expected hazardous weather 406b, and landing 406c. In some implementations, a critical event can be added to the predicted fatigue profile 400 during the flight in response to the detection of a new critical event. For example, an unexpected hazardous weather event that is detected during the flight after takeoff can be added to the predicted fatigue profile 400.

Figure 6:
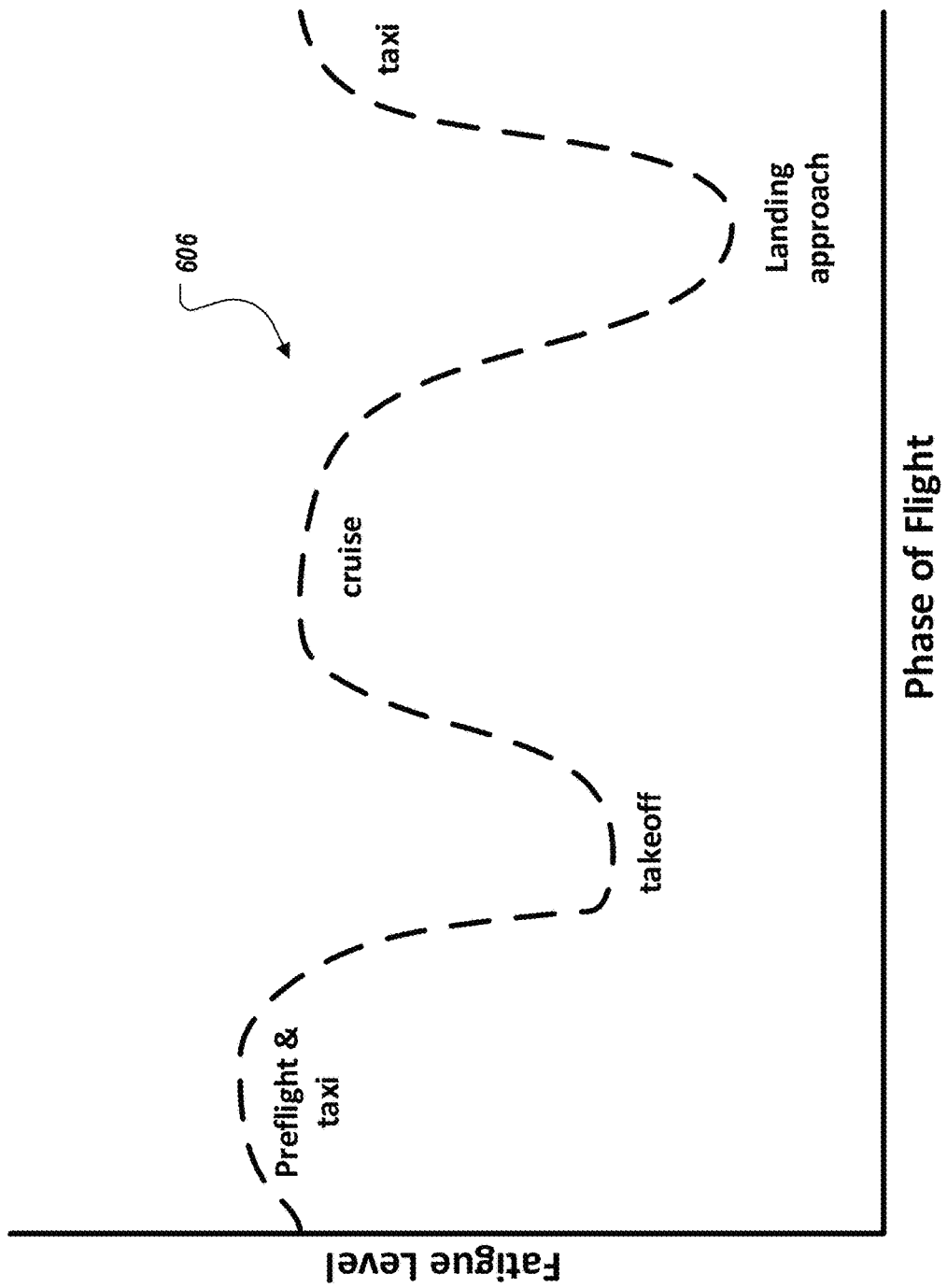
FIG. 6 is diagram of a dynamic fatigue threshold for a flight generated by a flight risk management application in accordance with example implementations.

The predicted fatigue profile 400 also includes a threshold fatigue level 404. In some implementations, the threshold fatigue level 404 represents a level of fatigue above which a flight crew member's ability to manage a critical event is diminished. In some implementations, the threshold fatigue level 404 is dynamic and is adjusted based on the estimated level of fatigue required for each portion of the flight. For example, during critical events 406a, 406b, 406c, such as takeoff and landing, the threshold fatigue level can be higher compared to other portions of the flight to account for the increased flight crew attention required during the critical events 406a, 406b, 406c. FIG. 6 depicts a dynamic fatigue threshold 606 that is adjusted based on the level of risk, and corresponding attention required, for various portions of a flight.

In some implementations, the predicted fatigue profile is generated by applying a fatigue prediction model that correlates sleep and fatigue levels to a sleep history for a period of time for the flight crew member. In some implementations, the sleep history for a period of time for the flight crew member is determined based on the flight history for the flight crew member for the period of time. For example, as previously discussed, the sleep history for the pilot can be estimated based on the pilot's work schedule, including the flights recently operated by the pilot. After predicting the pilot's sleep history, a predicted fatigue profile can be generated for the pilot by applying a fatigue prediction model correlating sleep and fatigue to the pilot's predicted sleep history. In some implementations, the fatigue prediction model accounts for the time of day during which the flight will occur in predicting the level of fatigue for a flight crew member. In some implementations, a two-process fatigue prediction model is applied to the flight crew member's sleep history to determine the flight crew member's predicted level of fatigue throughout the flight.

In some implementations, the predicted fatigue profile is determined based on a plurality of group fatigue profiles and the history information obtained for the flight crew member, including fatigue interventions performed by the flight crew member to prepare for the flight. As described in further detail below, group fatigue profiles can be generated by comparing the history information for a plurality of test subjects, including fatigue interventions performed by the test subjects, to the actual fatigue levels of the respective test subjects, and determining correlations between the history information and the measured fatigue levels. For example, a plurality of test subjects can submit their history information, including rest wake activity and flight schedules for a specified period of time, as well as fatigue interventions taken by the test subjects, such as consumption of caffeine, and the actual fatigue levels of the respective test subjects can be observed during a flight or a flight simulation.

In some implementations, test subjects are categorized based on their history information. For example, test subjects with 7 or more hours of sleep in the last 24 hours, fewer than 50 flying hours in the last seven days, and caffeine consumed in the last 4 hours are categorized as "Group 1," test subjects with less than 7 hours of sleep in the last 24 hours or more than 50 flying hours in the last seven days and caffeine consumed in the last 4 hours are categorized as "Group 2," and test subjects with less than 7 hours of sleep in the last 24 hours and more than 50 flying hours in the last seven days and no caffeine consumed in the last 4 hours are categorized as "Group 3." The group fatigue profiles can be generated by averaging the fatigue levels of test subjects in each of the respective groups. For example, a first group fatigue profile is generated by averaging the fatigue levels observed for the test subjects categorized as "Group 1" and a second group fatigue profile is generated by averaging the fatigue levels observed for the test subjects categorized as "Group 2."

In some implementations, the predicted fatigue profile for a flight crew member is obtained by comparing the history information for the respective flight crew member with the history information categories associated with each of the group fatigue profiles, and selecting the group fatigue profile for the category that most closely matches the history information for the respective flight crew member. For example, if the history information for the flight crew member indicates that the flight crew member has slept 6 hours in the last 24 hours, has flown 55 hours in the last seven days, and has not consumed any caffeine in the last 4 hours, then, based on the above-described group fatigue profile categories, the group fatigue profile generated for "Group 3" will be selected as the predicted fatigue profile of the flight crew member. In contrast, if, for example, the history information for the flight crew member indicates that the flight crew member has slept 9 hours in the last 24 hours, has flown 30 hours in the last seven days, and has consumed caffeine in the last 4 hours, then, based on the above-described group fatigue profile categories, the group fatigue profile generated for "Group 1" will be selected as the predicted fatigue profile for the flight crew member.

Figure 4B:
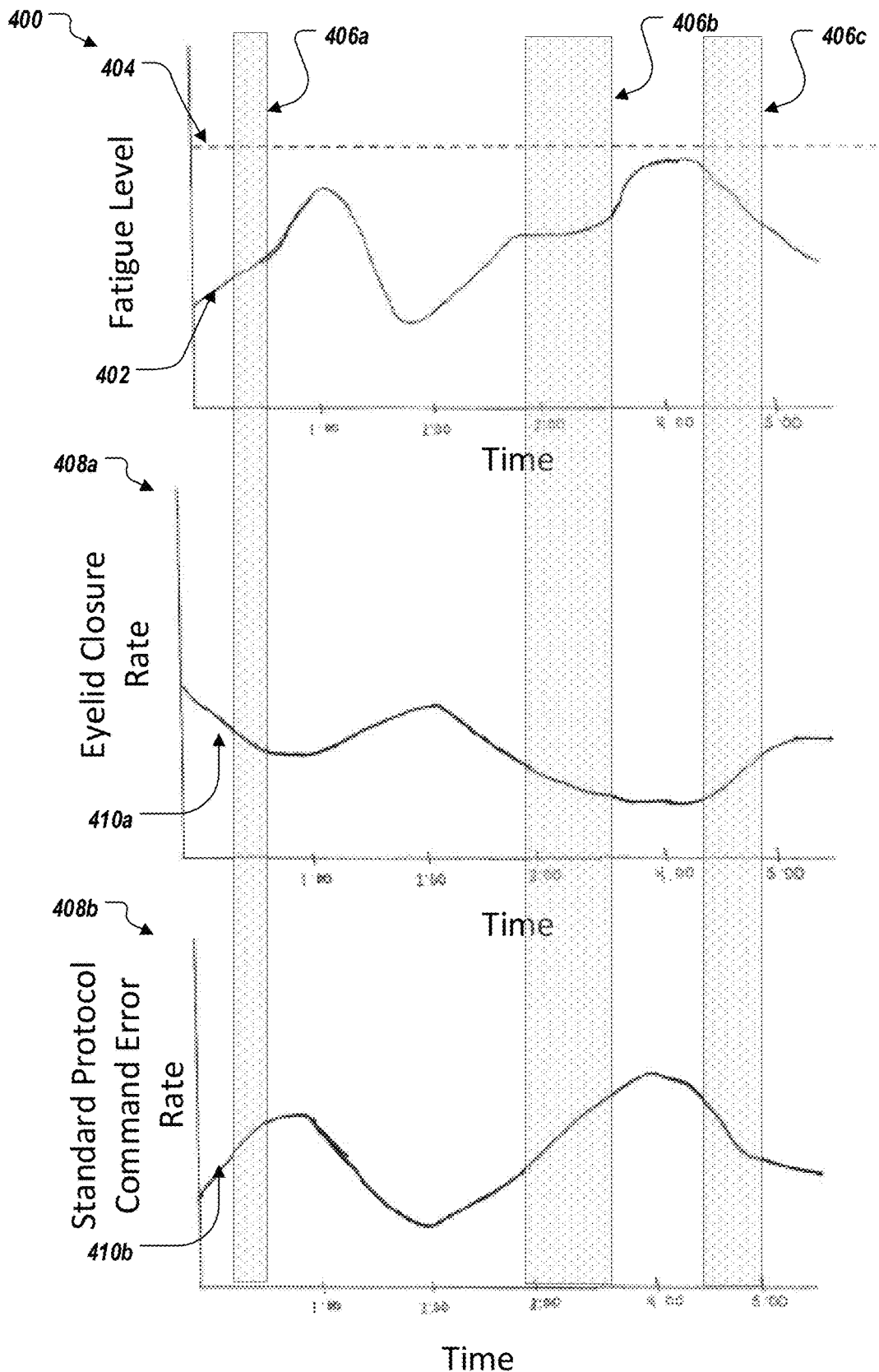

One or more fatigue indicator profiles are generated for the flight crew member (308). FIG. 4B depicts exemplary fatigue indicator profiles 408a, 408b. The one or more fatigue indicator profiles 408a, 408b depict the predicted fatigue indicator values 410a, 410b for a user for each of the respective fatigue indicators over a period of time. In some implementations, the one or more fatigue indicator profiles generated for the flight crew member represent the expected values 410a, 410b of one or more measureable fatigue indicators for the flight crew member over the duration of the flight based on the crew members predicted fatigue profile. For example, fatigue indicator profile 408a depicts the expected eyelid closure rate 410a for a pilot over the duration of the flight and fatigue indicator profile 408b depicts the expected standard protocol command error rate 410 for the pilot over the duration of the flight.

The one or more fatigue indicator profiles 408 can also include one or more critical event indicators 406. In some implementations, the one or more fatigue indicator profiles 408 include the same critical event indicators 406 as the critical event indicators 406 included in the predicted fatigue profile 400. For example, predicted fatigue profile 400, fatigue indicator profile 408a, and fatigue indicator profile 408b each include a critical event indicator corresponding to takeoff 406a, expected hazardous weather 406b, and landing 406c. That is, the critical event indicators 406 can be applied to the flight indicator profiles 408 in a manner similar to that described above in reference to the predicted fatigue profile 400.

As described in further detail below, the one or more fatigue indicator profiles can be determined based on the predicted fatigue profile determined for the flight crew member. Further, the one or more fatigue indicator profiles can be generated based on a correlation between actual fatigue levels and fatigue indicator values. In some implementations, the one or more fatigue indicator profiles are generated by a risk management application executed by an onboard computing device (e.g. risk management application 144b stored on IRM computing device 150 of FIG. 2). In some implementations, the one or more fatigue indicator profiles are generated by a risk management application stored on a remote device (e.g. risk management application 144a stored on server 102 of FIG. 2).

Figure 3B:
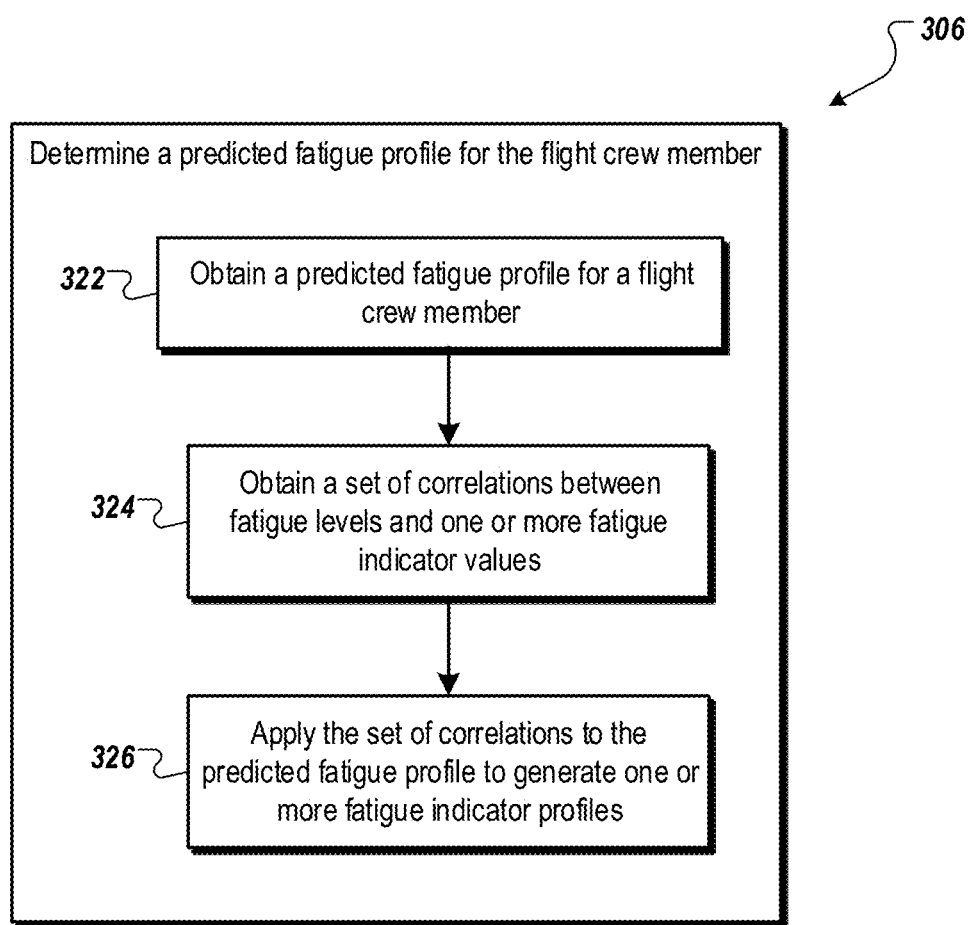
FIG. 3B is a flowchart for an example process for generating user fatigue profiles in accordance with an example implementations.

FIG. 3B depicts a flowchart of an example process 306 for determining fatigue indicator profiles based on a predicted fatigue profile. In some implementations, the process 306 can be provided as one or more computer-executable programs executed using one or more computing devices. In some examples, the process 306 is executed by a system, such as IRM system 200 of FIG. 2. In some implementations, all or portions of process 306 can be performed on a remote computing device, a server system, or a cloud-based server system. For example, all or portions of process 300 can be performed by a computing device that is located within a vehicle (e.g., IRM computing device 150 located on aircraft 204 of FIG. 2).

A predicted fatigue profile for a flight crew member is obtained (322). As previously described, in some implementations, predicted fatigue profiles are generated based on applying a fatigue model to the history information, such as flight history information, received from the flight crew member. In some implementations, predicted fatigue profiles are generated based on the history information for a flight crew member and a set of group profiles. In some implementations, the predicted fatigue profile is obtained by an onboard computing device (e.g., IRM computing device 150 of FIG. 2). In some implementations, the predicted fatigue profile is generated by a risk management application executed by the onboard computing device. In some implementations, a server (e.g., server 102 of FIG. 2) generates the predicted fatigue profiles based on the history information for a flight crew member. The server can then send the predicted fatigue profile to the computing device. In some implementations, a server obtains the predicted fatigue profile for the flight crew member from another computing device.

A set of correlations between fatigue levels and one or more fatigue indicators is obtained (324). In some implementations, the set of correlations between fatigue levels and one or more fatigue indicator values is obtained by a computing system of a vehicle (e.g., IRM computing device 150 on aircraft 204 of FIG. 2). In some implementations, the set of correlations is stored on IRM computing device 150. In some implementations, IRM computing device 150 obtains the set of correlations from another computing device (e.g., server 102 of FIG. 2).

In some implementations, the set of correlations between fatigue level and measured fatigue indicators is generated by measuring the actual fatigue levels and one or more fatigue indicator values for a plurality of test subjects over a period of time (e.g., during a flight or a flight simulation) to determine a set of correlations between the measured fatigue levels and measured fatigue indicator values. The actual fatigue levels of the test subjects can be determined based on electroencephalogram (EEG) measurements and reaction time test results for each of the test subjects. The one or more fatigue indicator values observed for the test subjects can be compared to the measured fatigue levels for the respective test subjects to determine a correlation between fatigue level and observed fatigue indicator values. For example, the fatigue level of each test subject of the plurality of the test subjects can be compared with the number of eyelid closures per minute for each of the respective test subjects to determine a correlation between the rate of eyelid closures and fatigue level.

The set of correlations between fatigue levels and the fatigue indicator values is applied to the predicted fatigue profile for a flight crew member to generate one or more fatigue indicator profiles for the flight crew member (326). For example, based on a correlation observed between fatigue level and the rate of eyelid closures for the plurality of test subjects, a fatigue indicator profile representing the expected rate of eyelid closures for the flight crew member over the course of a flight can be generated by applying the correlation to the predicted fatigue profile generated for the flight crew member.

In some implementations, one or more fatigue indicator profiles can be generated for a flight crew member for one or more respective fatigue indicators. In some implementations, fatigue indicator profiles can be generated based on one or more fatigue indicators related to eye movement such as rate of eyelid closures, length of eyelid closure, fixation of gaze, eye scanning, and like eye movements. In some implementations, fatigue indicator profiles can be generated based on one or more fatigue indicators related to leg movement, such as rate of leg movement and rate of weight shifting. In some implementations, fatigue indicator profiles can be generated based on one or more fatigue indicators related of human physiology metrics, such as pulse, blood pressure, rate of breathing, body temperature, sleep wake patterns, and other like physiological indicators. In some implementations, fatigue indicator profiles can be generated based on one or more fatigue indicators related audio data received from the crew member. For example, fatigue indicator profiles can be generated based on the rate of errors in a set of standard protocol command litanies performed by a flight crew member.

In some implementations, the one or more fatigue indicator profiles can be generated in part based on prior predicted fatigue profiles and measured fatigue indicator values generated for the flight crew member for previous flights piloted by the flight crew member. For example, correlations between the flight crew member's previous fatigue profiles and respective measured fatigue indicator values captured by fatigue indicator sensors during previous flights operated by the flight crew member can be used to improve the accuracy of the one or more fatigue indicator profiles by providing additional information that strongly correlates the flight crew member's level of fatigue with the various fatigue indicators.

In some implementations, the history information can include the measured fatigue indicator values and the fatigue profiles generated for the flight crew member over several flights worked by the flight crew member over a predetermined period of time (e.g., 12 hours, 24 hours, etc.). FIG. 7 depicts a fatigue profile for a flight crew generated over a predetermined period of time (e.g., the previous 24 hour time period) that includes the fatigue profiles 710, 712, 714 generated during the three flights worked by the flight crew member during the time period, as well as the predicted fatigue levels 720, 722 of the flight crew member during periods of rest between each of the flights. The fatigue profiles 710, 712, 714 are generated based on fatigue indicator sensor data collected during the respective flights. By including one or more of the fatigue profiles 710, 712, 714 generated during recent flights worked by the flight crew member, as well as the measured fatigue indicator values corresponding to the fatigue profiles 710, 712, 714, in the data analyzed by the machine learning model to generate the one or more fatigue indicator profiles, the accuracy of the fatigue indicator profiles generated for the flight crew member for an upcoming flight can be improved.

In some implementations, one or more machine learning techniques are used to generate the predicted fatigue profile and the one or more fatigue indicator profiles for the flight crew member. For example, based on test data (such as the fatigue data for test subjects described above), as well as the flight information and the history information obtained for the flight crew member, including the flight crew member's previous work schedule, a machine learning algorithm can be used to determine the predicted fatigue profile and fatigue indicator profiles for the flight crew member.

A variety of machine learning techniques can be employed to generate the predicted fatigue profile and the one or more fatigue indicator profiles for the flight crew member. For example, in some implementations, a time series analysis of the history information and flight information for the flight crew member may be performed to determine a predicted fatigue profile for the flight crew member. Several types of time series analyses can be utilized, such as clustering time series analysis, including subsequence clustering. In addition, in training a machine learning model to predict fatigue, a variety of variables related to fatigue can be analyzed using time series analysis. Example types of data that can be analyzed using time series analysis to train a fatigue prediction machine learning model include, but are not limited to, data regarding whether a flight crew member was awake or asleep during portions of a duty schedule, the predicted fatigue for a flight crew member over the course of a duty schedule of one or more flights, measured alertness of a flight crew member over the course of a duty schedule of one or more flights, and the predicted risk for a flight. The data used in time series analysis for training a machine learning model to predict fatigue can include time series data, cross sectional data, or a combination of both (i.e., "pooled data").

Using subsequence clustering, in a given time series T of length m, a subsequence Cp of T is a sampling of length w<m of contiguous positions from T, that is C=tp . . . tp+w−1 for 1<=p<=m−w+1. Sliding windows of length w can be extracted from the time series T of length m, and a matrix S of all possible subsequences can be built across T, with subsequence Cp being positioned in the pth row of S. The size of the matrix S generated using subsequence clustering is (m−w+1) by w.

The sampling length (w) used for subsequence clustering may be indicative of a length of time useful for predicting fatigue. For example, in some implementations, w is set to 24 hours and is calculated from 16 hours before the end of the flight crew member's scheduled work duty to 8 hours after the end of the flight crew member's scheduled work duty. This sampling length w encompasses both potential sleep preparation for duty performed by the flight crew member and also recovery from the duty. In some implementations, w is set to 24 hours before the end of the flight crew member's scheduled work duty to 24 hours after the end of the flight crew member's scheduled work duty.

Time series clustering enables the detection of anomalies in data, such as anomalies in the history information for a flight crew member. For example, once a cluster representing a particular sleep pattern is identified based on performing time series analysis of training data related to flight crew member sleep, the history information for a particular flight crew member can be analyzed using time series clustering to determine whether the history information includes a sleep pattern outside the clusters (i.e., outside the typical or expected sleep patterns), which can be predictive of increased levels of fatigue.

In some implementations, a K-means algorithm can be used to partition history information and/or the flight information for a flight crew member into clusters for time series analysis, and subsequent generation of a fatigue prediction profile and fatigue indicator profile(s). Using this technique, centroids are formed for each of the clusters, and the sum of the squared distance between the data points and each cluster's centroid is kept at minimum. For example, the K-means algorithm can be used to generate a scatter plot of all of the flights performed by one or more flight crew members with the x axis representing the duty period start time and the y axis representing the length of the duty period, and clusters between the plotted flights can be identified. In order to utilize the K-means algorithm, a value for the number of clusters (k) must be defined. Once k is defined, the k cluster centers are initialized, and each object (e.g., each previous flight performed by the flight crew member) is assigned to the nearest cluster center based upon the mapping the object. Once each object is assigned to a cluster, the k cluster centers are re-estimated based on the plotted data objects and their respective cluster assignments. The clusters generated using the K-means algorithm are typically non-overlapping. For instance, a particular work duty or flight operated by the flight crew member can only be assigned to a single cluster when the clusters are formed using a K-means algorithm In some implementations, hierarchical clustering can be used to partition the history information and/or flight information for the flight crew member into clusters for time series analysis and subsequent generation of a fatigue prediction profile and fatigue indicator profile(s). With hierarchical clustering, it is not necessary to define the number of clusters (k). For hierarchical clustering, the distance between each of the data objects (e.g., previous flight performed by the flight crew member) is calculated. A matrix containing each of these distance calculations is formed, and the two most similar data objects are identified. The two data objects identified as being most similar based on the distance calculations are then joined to form a cluster. This process is then repeated until all of the data objects are contained within a single cluster.

Referring again to FIG. 3A, one or more measured fatigue indicator values associated with the flight crew member are obtained during the flight (310). In some implementations, the one or more measured fatigue indicator values associated with the flight crew member are obtained from at least one sensor in an aircraft. For example, an onboard computing device (e.g., onboard IRM computing device 150 of FIG. 2) can obtain one or more measured fatigue indicator values from at least one sensor in the aircraft that the flight crew member (e.g., user 206 of FIG. 2.) is piloting. In some implementations, a computing device sends a request for fatigue indicators values to the at least one sensor and receives the fatigue indicator values in response to the request (e.g., "pulls" the indicator values). For example, a computing device can periodically request measured fatigue indicator values from the at least one sensor (e.g., sensors 208-214 of FIG. 2) periodically over the course of a flight. In some implementations, the at least one sensor sends measured fatigue indicator values to a computing device without having received a request (e.g., "pushes" the indicator values). For example, sensors 208-214 can proactively send fatigue indicator values measured by the respective sensors to a computing device periodically throughout the duration of a flight.

The at least one sensor can include one or more eye tracking sensors (e.g., eye tracking sensors 208 of FIG. 2). The at least one sensor can include one or more leg motion sensors (e.g., leg motion sensors 210 of FIG. 2). The at least one sensor can include one or more human physiology sensors (e.g., human physiology sensors 212 of FIG. 2). The at least one sensor can include one or more audio sensors (e.g., the audio sensors 214 of FIG. 2).

The one or more measured fatigue indicator values associated with the flight crew member include, but are not limited to, rate of eyelid closures, length of eyelid closure, fixation of gaze, eye scanning, rate of leg movement, rate of weight shifting, pulse, blood pressure, rate of breathing, body temperature, and rate of errors in standard protocol commands. In some implementations, the fatigue indicator values obtained correlate to one or more fatigue indicators represented by the one or more fatigue indicator profiles (e.g., fatigue indicator profiles 408a, 408b) generated for the flight crew member.

Figure 4C:
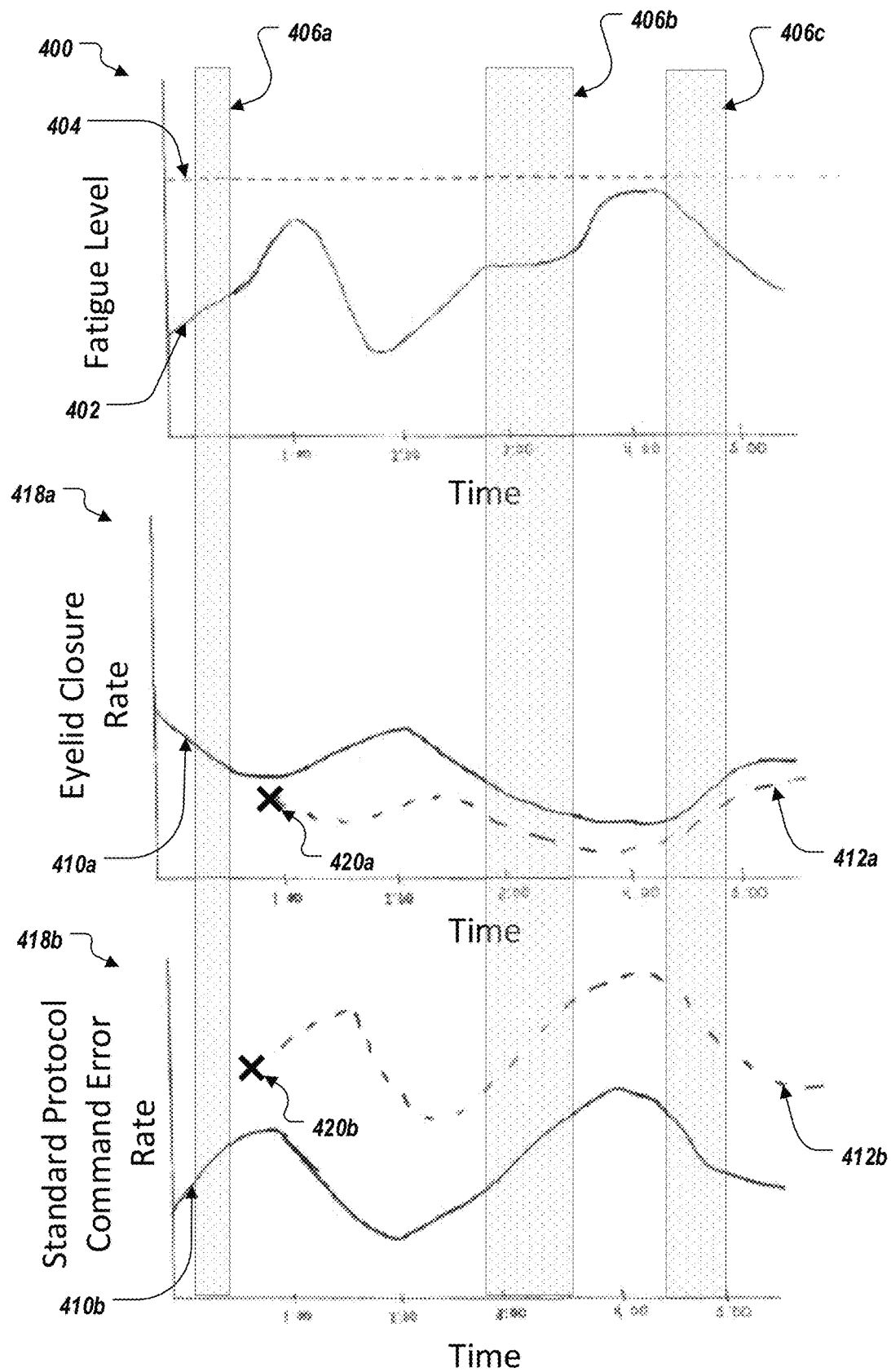

One or more updated fatigue indicator profiles for the flight crew member are generated (312). FIG. 4C depicts updated fatigue indicator profiles 418a, 418b. The updated fatigue indicator profiles 418a, 418b include updated predicted fatigue indicator values 412a, 412b for the user for each of the respective fatigue indicators over a period of time. For example, the one or more updated fatigue indicator profiles 418a, 418b include the expected values for the respective fatigue indicators 412a, 412b for the pilot for the remainder of the flight that the pilot is currently piloting.

As described in further detail below, the one or more updated fatigue indicator profiles can be generated based on the one or more fatigue indicator values obtained from the at least one sensor. In some implementations, the one or more fatigue indicator profiles 408a, 408b are updated based on corresponding fatigue indicator values 420a, 420b obtained from a sensor that measures the fatigue indicator represented by the respective fatigue indicator profile. For example, fatigue indicator profile 408a, which represents the flight crew member's expected rate of eyelid closures over the course of a flight, can be updated based on a measured rate of eyelid closures 420a for the flight crew member obtained from at least one sensor measuring eye movement (e.g., eye tracking sensors 208 of FIG. 2). In some implementations, the updated fatigue indicator profiles 418a, 418b are generated by a risk management application executed by an onboard computing device. In some implementations, the updated fatigue indicator profiles 418a, 418b are generated a risk management application executed by server communicably coupled to the at least one sensor. In some implementations, the updated fatigue indicator profiles 418a, 418b are generated by processing the measured fatigue indicator values 420a, 420b received from the at least one sensor using a trained machine learning model stored on a computer (e.g. IRM computing device 150 of FIG. 2).

In some implementations, the one or more updated fatigue indicator profiles are generated in response to a determination that a respective measured fatigue indicator value has deviated more than a threshold amount. For example, if the rate of eyelid closures 420a measured for the pilot by an onboard sensor at a certain time during the flight has deviated more than a threshold amount from the predicted rate of eyelid closures 410a for that time during the flight according to the fatigue indicator profile 408a for expected rate of eyelid closures, then an updated fatigue indicator profile 418a with an updated expected rate of eyelid closure 412a for the remainder of the flight is generated. In contrast, if the rate of eyelid closures 420a measured for the pilot by an onboard sensor at a certain time during the flight has deviated from the predicted rate of eyelid closures 410a for that time according to the fatigue indicator profile 408a, but less than threshold amount, an updated fatigue indicator profile 418a for eyelid closure rate will not be generated. In some implementations, the threshold amount of deviation allowable prior to replotting is predetermined for each fatigue indicator.

Figure 4D:
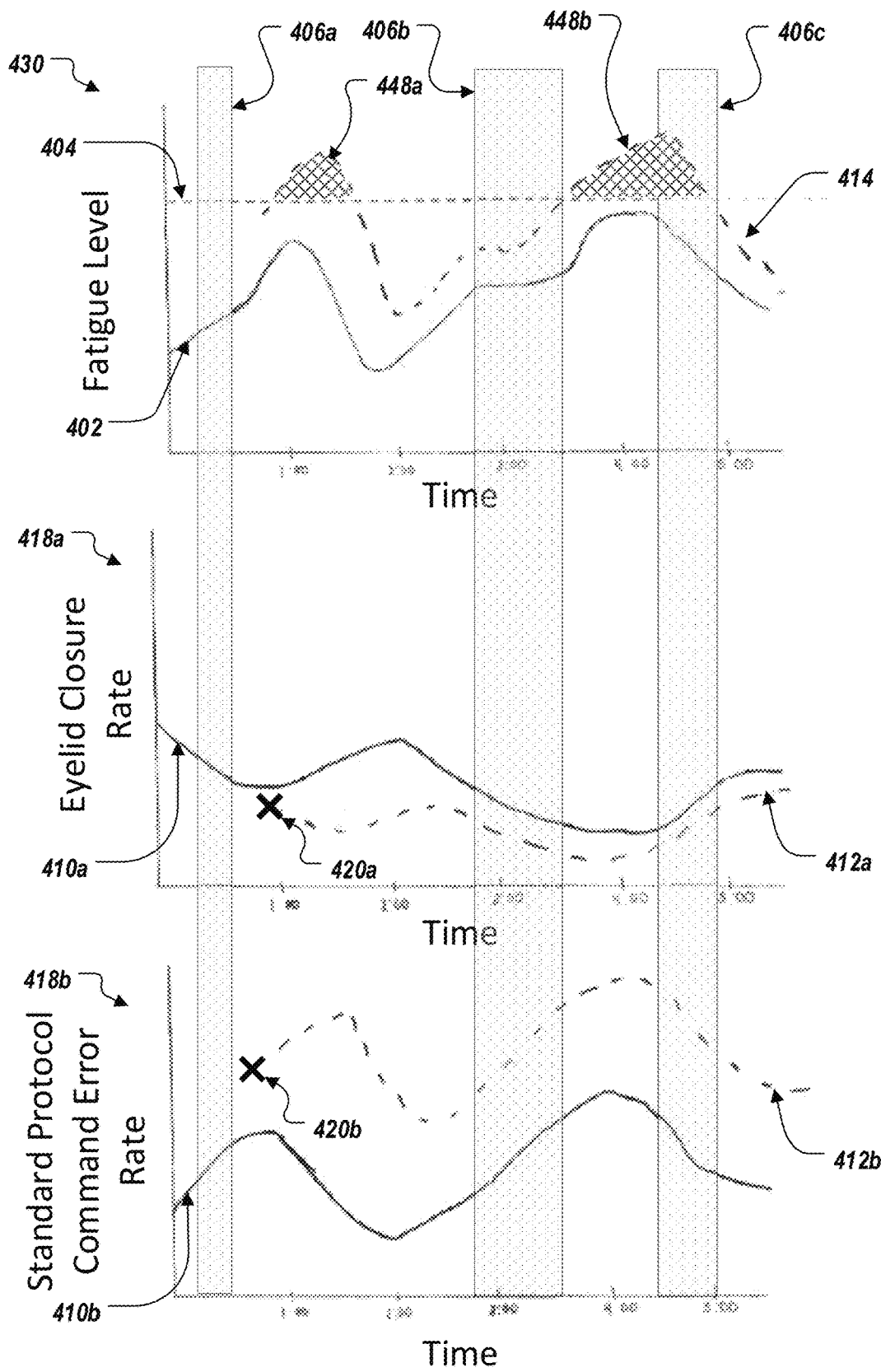

An updated predicted fatigue profile for the flight crew member is generated (314). FIG. 4D depicts an exemplary updated fatigue profile 430. The updated predicted fatigue profile 430 depicts the user's updated predicted level of fatigue 414 over a period of time. For example, the updated predicted fatigue profile 430 depicts a pilot's updated predicted level of fatigue 414 for the remainder of the flight.

As described in further detail herein, the updated predicted fatigue profile can be generated based on the one or more updated fatigue indicator profiles (e.g., updated fatigue indicator profiles 418a, 418b). For example, deviations between the predicted fatigue indicator values 410a, 410b in the fatigue indicator profiles 408a, 40b and predicted fatigue indicator values 412a, 412b in the updated fatigue indicator profiles 418a, 418b generated based on the measured indicator values 420a, 420b indicate a deviation in actual fatigue levels from those originally predicted in the predicted fatigue profile 400.

In some implementations, an updated fatigue indicator profile is generated when a predetermined number of measured fatigue indicators deviate from their respective predicted fatigue indicator profiles. For example, if a particular cockpit incorporates three different types of fatigue indicators (e.g., eyelid closure rate, standard command protocol error rate, and heart rate) updated fatigue indicator profiles may only be generated when two out of the three measured fatigue indicator values deviate from their respective fatigue indicator profiles by a threshold amount of deviation. Replotting the fatigue indicator profiles and/or the predicted fatigue profile only in response to multiple measured fatigue indicators deviating from respective indicator profiles may help account for noise in the predicted fatigue profile by minimizing the effects of outlier measured fatigue indicator values (i.e., filtering out noise). For instance, there may be no need to replot a predicted fatigue profile and/or fatigue indicator profiles if only a pilot's measured eyelid closure rate is deviating from the eyelid closure rate profile. For example, the pilot may simply have dry contacts causing him or her to blink more rapidly. However, if both the pilot's measured eyelid closure rate and measured heart rate are deviating from their respective indicator profiles, then there is a greater likelihood that the deviation of both measured indicators is due to unexpected fatigue and replotting the pilot's fatigue indicator profiles and/or predicated fatigue profile is appropriate.

In some implementations, the fatigue indicator profiles are weighted or prioritized based on the strength of the correlation between the specific fatigue indicator and actual fatigue levels. These weightings can be applied to observed deviations between the measured fatigue indicator values and the predicted values in the respective fatigue indicator profiles to determine whether a threshold amount of deviation has occurred to trigger generation of an updated predicted fatigue profile. For example, fatigue indicators related to eye movement and heart rate can be more heavily weighted than other indicators as they may be more strongly correlated to fatigue. In such examples, higher weightings applied to deviations in the eye movement and heart rate of a flight crew member will be more likely to trigger generation of an updated fatigue indicator profile than another, lesser weighted, indicators (e.g., leg movement). Weighting fatigue indicators based on the strength of the correlation between each indicator type and fatigue levels helps minimize the effects of outlier measured fatigue indicator values (i.e., helps reduce noise).

In some implementations, the measured fatigue indicator values can be compared with one another to more accurately predicted fatigue. For example, audio data can be compared with data from one or more eye tracking sensors to determine if the flight crew member is looking at the correct portion of the cockpit during a command checklist. In some implementations, combining and comparing several measured fatigue indicator values provides a stronger prediction of fatigue.

In some implementations, the updated predicted fatigue profile 430 is generated by applying a set of correlations between one or more fatigue indicator values and fatigue levels to the one or more updated fatigue indicator profiles 418a, 418b. For example, as depicted in FIG. 4D, if the updated fatigue indicator profile for expected rate of eyelid closures 418a indicates a lower rate of eyelid closures than previously predicted, and a lower rate of eyelid closures is correlated with increased levels of fatigue, then an updated predicted fatigue profile 430 is generated, the updated predicted fatigue profile 430 having increased levels of fatigue 414 during the periods of time corresponding to a decreased rate of eyelid closures in the updated fatigue indicator profile 418a.

In some implementations, the updated predicted fatigue profile can be generated in part based on prior predicted fatigue profiles and one or more measured fatigue indicator values for the flight crew member from previous flights piloted by the flight crew member. For example, correlations between the flight crew member's previous predicted fatigue profiles and respective measured fatigue indicator values for prior flights can be applied to the one or more updated fatigue indicator profiles for the flight crew member to tailor the updated predicted fatigue profile based on the flight crew member's previous fatigue indicator values and predicted fatigue.

Figure 3C:
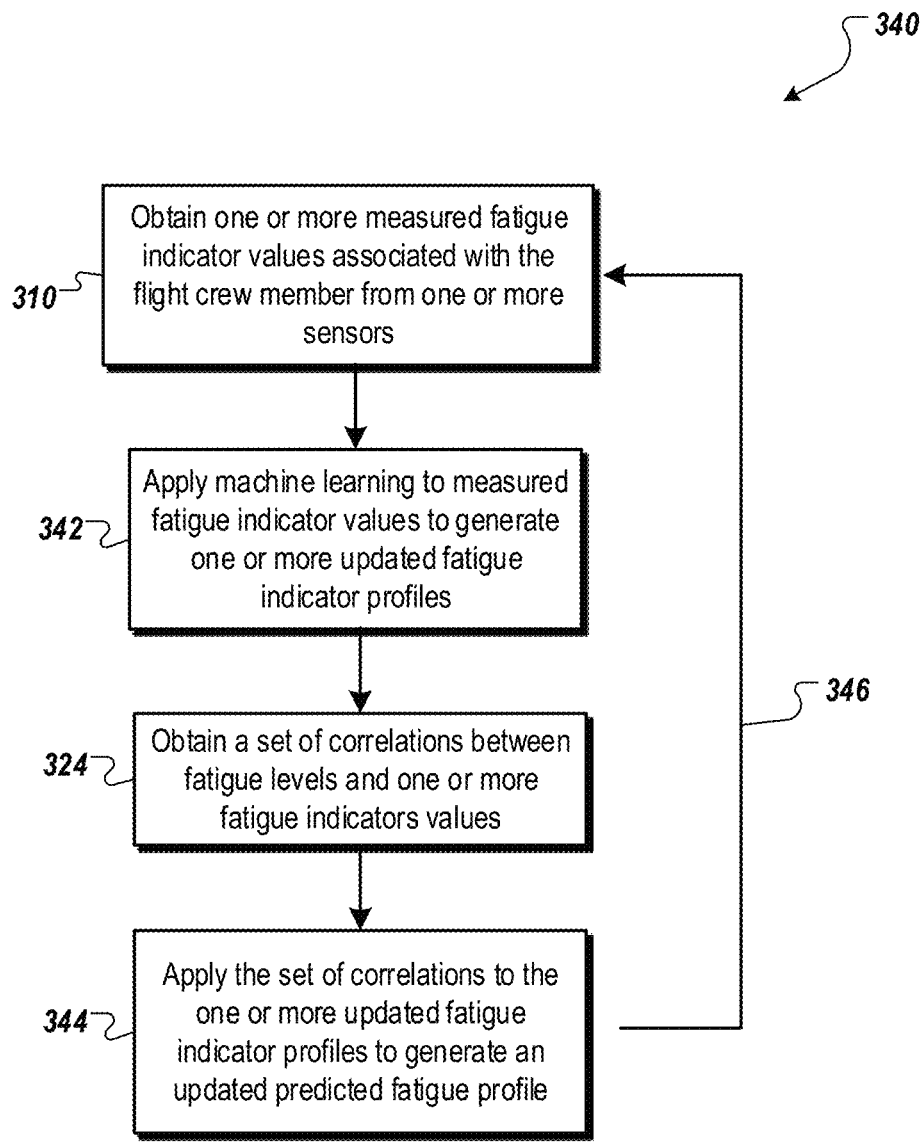
FIG. 3C is a flowchart for an example process for updating user fatigue profiles in accordance with an example implementations.

FIG. 3C depicts a flowchart of an example process 340 for generating updated fatigue indicator profiles and updated predicted fatigue profiles. In some implementations, the process 340 can be provided as one or more computer-executable programs executed using one or more computing devices. In some examples, the process 340 is executed by a system, such as IRM system 200 of FIG. 2. In some implementations, all or portions of process 340 can be performed on a remote computing device, a server system (e.g., server 102 of FIG. 2), and a cloud-based server system. For example, all or portions of process 340 can be performed by a computing device that is located within a vehicle (e.g., IRM computing device 150 located on aircraft 204 of FIG. 2).

One or more measure fatigue indicator values are obtained from one or more sensors (310). As previously discussed, in some implementations, the one or more measured fatigue indicator values associated with the flight crew member are obtained from at least one sensor in an aircraft. For example, an onboard computing device can receive one or more measured fatigue indicator values over a network from at least one sensor in the aircraft that the flight crew member (e.g., user 206) is piloting.

Machine learning is applied to the measured fatigue indicator values to generate one or more updated fatigue indicator profiles (342). In some implementations, the updated fatigue indicator profiles are generated by processing the measured fatigue indicator values received from the at least one sensor using a trained machine learning model stored on a computer (e.g., IRM computing device 150 of FIG. 2). Machine learning models used to process the measured fatigue indicator values to generate updated fatigue indicator profiles can include Bayesian optimization, deep neural networks, or Markov chain methods. As previously discussed, in some implementations, the one or more fatigue indicator profiles are generated in response to a determination that a respective measured fatigue indicator value has deviated more than a threshold amount of deviation. A set of correlations between fatigue levels and one or more fatigue indicator values is obtained (324). As previously discussed, actual fatigue levels and one or more measured fatigue indicator values can be obtained for a plurality of test subjects over a period of time (e.g., during a flight or a flight simulation). The one or more fatigue indicator values observed for the plurality test subjects can be compared to the measured fatigue levels for the respective test subjects to determine a correlation between fatigue levels and observed fatigue indicator values. In some implementations, the set of correlations between fatigue levels and one or more fatigue indicator values is obtained by a computing system of a vehicle (e.g., IRM computing device 150 on aircraft 204 of FIG. 2). In some implementations, the set of correlations is stored on IRM computing device 150. In some implementations, an onboard computing device obtains the set of correlations from another computing device (e.g., server 102 of FIG. 2).

The set of correlations between fatigue levels and one or more fatigue indicator values is applied to the one or more updated fatigue indicator profiles to generate an updated predicted fatigue profile for the flight crew member (344). For example, based on a correlation observed between fatigue levels and rates of eyelid closures for the plurality of test subjects, an updated predicted fatigue profile 430 can be generated by applying the correlation to the updated fatigue indicator profile 418*a* representing the updated expected rate of eyelid closures for the pilot. As previously discussed, in some implementations, an updated predicted fatigue profile is generated in response to more than a threshold amount of deviation occurring between the measured fatigue indicator values and the predicted fatigue indicator values in the fatigue indicator profiles.

In some implementations, the updated predicted fatigue profile can be generated in part based on prior predicted fatigue profiles and measured fatigue indicator values for the flight crew member from previous flights piloted by the flight crew member. For example, correlations between the flight crew member's previous predicted fatigue profiles and respective measured fatigue indicator values for prior flights can be applied to the one or more updated fatigue indicator profiles for the flight crew member to tailor the updated predicted fatigue profile based on the flight crew member's previous fatigue indicator values and predicted fatigue.

In some implementations, the updated predicted fatigue profile is generated by processing the one or more updated fatigue indicator profiles using a trained machine learning model stored on a computer (e.g., IRM computing device 150 of FIG. 2). In some implementations, the updated predicted fatigue profile is generated by processing the one or more updated fatigue indicator profiles, the flight crew member's prior predicted fatigue profiles, and the flight crew member's prior measured fatigue indicator values using a trained machine learning model stored on a computer (e.g., IRM computing device 150 of FIG. 2). Machine learning models used to generate the updated predicted fatigue profile can include Bayesian optimization, deep neural networks, or Markov chain methods.

In some implementations, the time series analysis and series clustering techniques described above in reference to generating the predicted fatigue profile and the predicted fatigue indicator profiles can be used to generate the updated predicted fatigue profiles and the updated fatigue indicator profiles. For example, one or more of the fatigue indicator values measured during the flight can be analyzed using a time series analysis and, based on this analysis, assigned to a cluster in a time series mapping of the respective type of fatigue indicator values to levels of fatigue. Based on the clusters that the measure fatigue indicator values are assigned to, the predicted fatigue for the flight crew member can then be determined based on the fatigue level corresponding to the assigned clusters. If the fatigue indicator values are assigned to clusters that corresponds with a fatigue level that is different than the current predicted fatigue level for the flight crew member based on the predicted fatigue profile for the flight crew member, this indicates that the predicted fatigue profile for the flight crew member may need to be updated. In addition, dynamic time warping can be used to improve the accuracy of the updated predicted fatigue profiles and updated fatigue indicator profiles and project the predicted fatigue profile and predicted fatigue indicator values for the flight crew member into the future.

In one example, the eyelid closure rate measured for a flight crew member during a flight can be analyzed in real time using time series analysis. Based on the time series analysis, the measured eyelid closure rate is assigned to a cluster in a time series mapping of eyelid closure rates to fatigue levels. Based on the cluster to which measured eyelid closure rate is assigned, the current fatigue level of the flight crew can be estimated. If the fatigue level estimated for the flight crew member using the time series analysis based on the measured eyelid closure rate is different than the predicted fatigue level indicated in the predicted fatigue profile for the flight crew member for the corresponding time period, the predicted fatigue profile for the flight crew member can be updated to reflect the estimated fatigue determined based on time series analysis of the measured rate of eyelid closure.

In some implementations, the process 340 of generating updated predicted fatigue profiles and updated fatigue indicator profiles is recursive, wherein the one or more updated fatigue indicator profiles and the updated predicted fatigue profile learn from one another (346). For example, as previously discussed, the predicted fatigue profile can be updated based on changes in the one or more updated fatigue indicator profiles by applying a correlation between one or more fatigue indicator values and actual fatigue to the one or more updated fatigue indicator profiles. Similarly, in some implementations, the one or more fatigue indicator profiles can be updated based on the updated predicted fatigue profile by applying a correlation between one or more fatigue indicator values and actual fatigue to the updated predicted fatigue profile. In some implementations, the one or more fatigue indicator profiles are updated multiple times throughout the duration of the flight in response to receiving measured fatigue indicator data. In some implementations, the updated predicted fatigue profile is updated multiple times throughout the flight in response to updates to the one or more fatigue indicator profiles.

In some implementations, one or more flight risk mitigation interventions are provided (316). In some implementations, the one or more flight risk mitigation interventions can be provided based on the updated fatigue profile generated for a flight crew member. For example, if an updated fatigue profile 430 indicates that a flight crew member is predicted to experience fatigue levels 414 above the threshold fatigue level 404 during a critical event 406, as shown in FIG. 4D at critical landing event 406c, then one or more flight risk mitigation interventions can be implemented to mitigate the risk posed by the crew member's predicted level of fatigue.

In some implementations, one or more flight risk mitigation interventions are provided based on the magnitude and duration of the flight crew member's predicted fatigue. For example, if an updated fatigue profile 430 indicates that a flight crew member is predicted to experience fatigue levels 414 above the threshold fatigue level 404 for longer than a threshold duration, a flight risk mitigation intervention is provided. In some examples, if updated fatigue profile 430 indicates that a flight crew member is predicted to experience fatigue levels 414 that are more than a threshold amount above the threshold fatigue level 404, a flight risk mitigation intervention is provided. In some implementations, a flight risk mitigation intervention is provided based on a combination of the magnitude and the duration of the flight crew member's predicted fatigue levels 414 above a threshold fatigue level 404. In some implementations, the magnitude and duration of the predicted fatigue levels of the flight crew member can be determined by calculating the area 448a, 448b under the predicted fatigue level 414 curve between the predicted fatigue level 414 and the threshold fatigue level 404, as shown in FIG. 4D.

In some implementations, flight risk mitigation interventions provided in process 300 include providing a warning to the flight crew member. For example, a warning can be provided to the flight crew member indicating that his or her predicted fatigue levels exceed threshold levels during a critical portion of the flight. In some implementations, warnings provided to flight crew members in response to high predicted fatigue levels include, but are not limited to, recommended methods for reducing fatigue, such as recommendations to consume caffeine and recommendations to stretch. In some implementations, a warning is provided to the flight crew member through a graphic user interface of an onboard computing device. In some implementations, a warning is provided to the flight crew member through a telecommunication device.

In some implementations, a warning is provided to the flight crew member based on the magnitude and duration of the flight crew member's predicted fatigue. For example, if an updated fatigue profile 430 indicates that a flight crew member is predicted to experience fatigue levels 414 above the threshold fatigue level 404 for longer than a threshold duration, a warning is provided to the flight crew member. In some examples, if updated fatigue profile 430 indicates that a flight crew member is predicted to experience fatigue levels 414 that are more than a threshold amount above the threshold fatigue level 404, a warning is provided to the flight crew member. In some implementations, a warning is provided to the flight crew member based on a combination of the magnitude and the duration of the flight crew member's predicted fatigue levels 414 above a threshold fatigue level 404.

In some implementations, flight risk mitigation interventions include automatically rerouting the flight to an alternate landing location. For example, if the predicted fatigue profile indicates that the flight crew member will be experiencing fatigue levels above a threshold level during the scheduled landing, the landing location can be automatically rerouted to a landing location that allows the flight crew member to land at a time when the flight crew member is predicted to be experiencing fatigue levels below the threshold fatigue level. In some implementations, the flight risk mitigation interventions include sending a request to the flight crew member to reroute the flight, and requiring the flight crew member to either accept or reject the request to reroute the flight.

In some implementations, the flight risk mitigation interventions include automatically engaging an autopilot function of the aircraft. For example, if the updated predicted fatigue profile indicates that the flight crew member will be experiencing fatigue above a threshold level during some portion of a flight, the autopilot function of the aircraft can be engaged automatically during the portions of the flight in which the predicted fatigue level of the flight crew member exceeds the threshold level. In some implementations, flight risk mitigation interventions include sending a request to the flight crew member to engage the autopilot function during periods of high predicted fatigue levels, and requiring the flight crew member to either accept or reject the request to engage the autopilot function.

In some implementations, the flight risk mitigation interventions include switching the control of the aircraft from the flight crew member to a remote operator. For example, if the updated predicted fatigue profile indicates that the flight crew member will experience fatigue levels above a threshold level, the control of the aircraft can be automatically switched from the flight crew member to a remote operator, such as ground control or another pilot that is located at a ground-based control location, during the portions of the flight in which the predicted fatigue level of the flight crew member exceeds a threshold level. In some implementations, another pilot remotely controlling the airplane is on stand-by at an airport. In some examples, another pilot remotely controlling the airplane is on stand-by at home and receives an automated message alerting the pilot to go to a remote piloting station (e.g., at an airport) to take remote control of the flight. In some implementations, the flight risk mitigation interventions include sending a request to the flight crew member and to a remote operator to switch the control of the aircraft from the flight crew member to the remote operator during periods of high predicted fatigue levels, and requiring both the flight crew member and the remote operator to either accept or reject the request to switch the control of the aircraft to the remote operator.

In some implementations, process 300 of producing a predicted fatigue profile and updating the predicted fatigue profile based on one or more measured fatigue indicator values is also performed for a remote operator. For example, another pilot that is located at a ground-based control location can remotely control the aircraft during the portions of the flight in which the predicted fatigue level of the flight crew member exceeds a threshold level. A predicted fatigue profile can be generated for the remote pilot based on the flight information and the history information for the remote pilot, and one or more fatigue indicator profiles can be generated based on the predicted fatigue profile for the remote pilot. One or more sensors located at the ground-based control location can measure one or more fatigue indicator values for the remote pilot. Based on the one or more fatigue indicators values, one or more updated fatigue indicator profiles can be generated for the remote pilot. In response to the one or more updated fatigue indicator profiles, an updated predicted fatigue profile can be generated for the remote pilot.

In some implementations, the flight risk mitigation interventions include alerting a second remote operator to take over control of the aircraft in response to determine that the current remote operator is experiencing fatigue above a threshold level. In some implementations, the flight risk mitigation interventions include switching the control of the aircraft back to a pilot located on the aircraft in response to determining that the current remote operator is experiencing fatigue above a threshold level and that the pilot on the aircraft is experiencing fatigue below the threshold level.

Figure 4E:
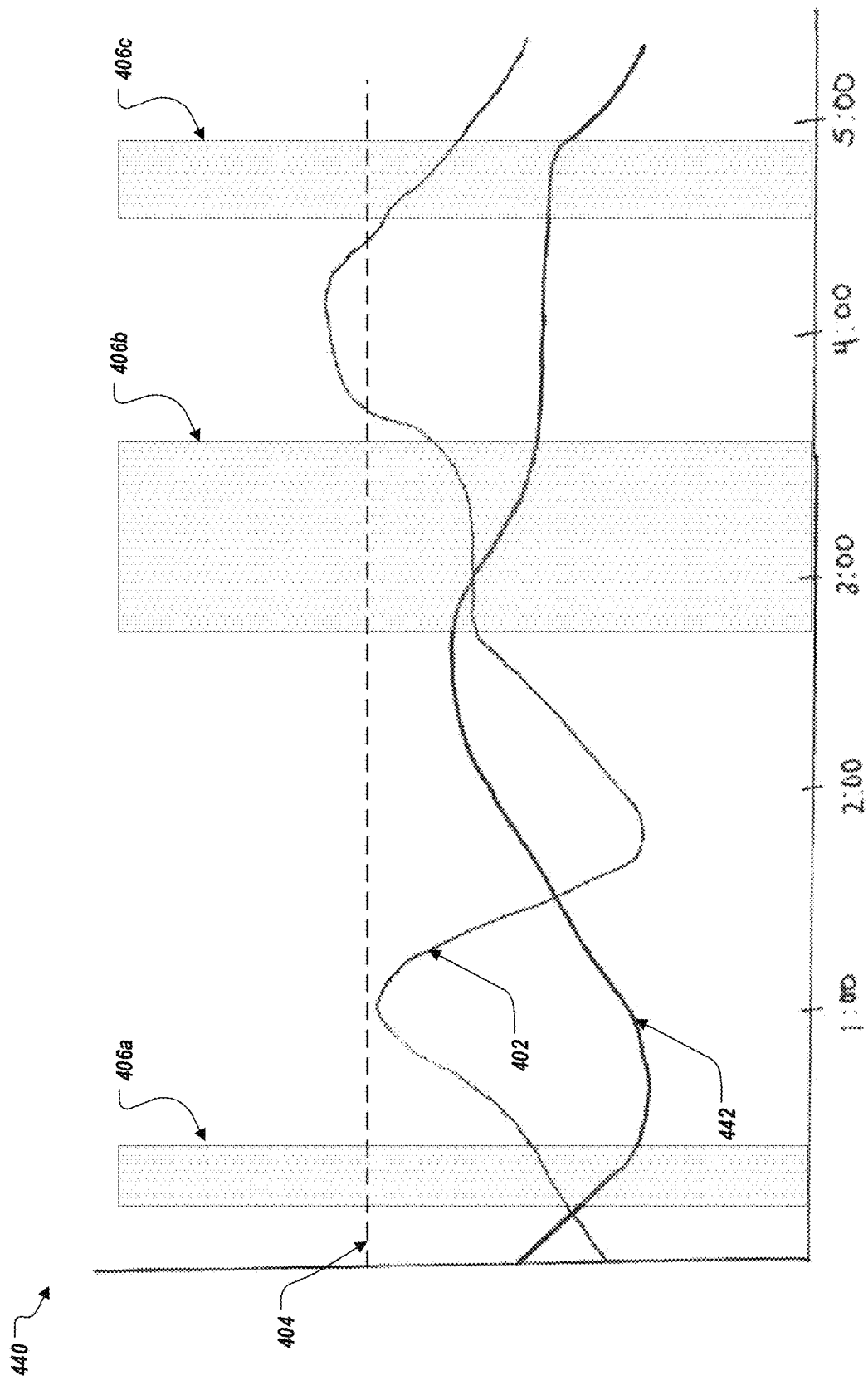

In some implementations, the updated predicted fatigue profiles of multiple flight crew members can be coordinated to determine the appropriate flight risk mitigation intervention. For example, predicted fatigue profiles and fatigue indicator profiles can be generated in steps 306 and 308 of process 300, respectively, for multiple flight crew members, such as a pilot and a co-pilot. FIG. 4E depicts a predicted fatigue profile 440 that includes the predicted level of fatigue 402 for a pilot and the predicted level of fatigue 442 for a co-pilot, based on the history information for the pilot and the co-pilot respectively. As can be seen in FIG. 4E, based on the predicted fatigue profile 440, both the pilot and the co-pilot are predicted to experience fatigue levels below the threshold level during each of the critical event 406 of the flight.

Figure 4F:
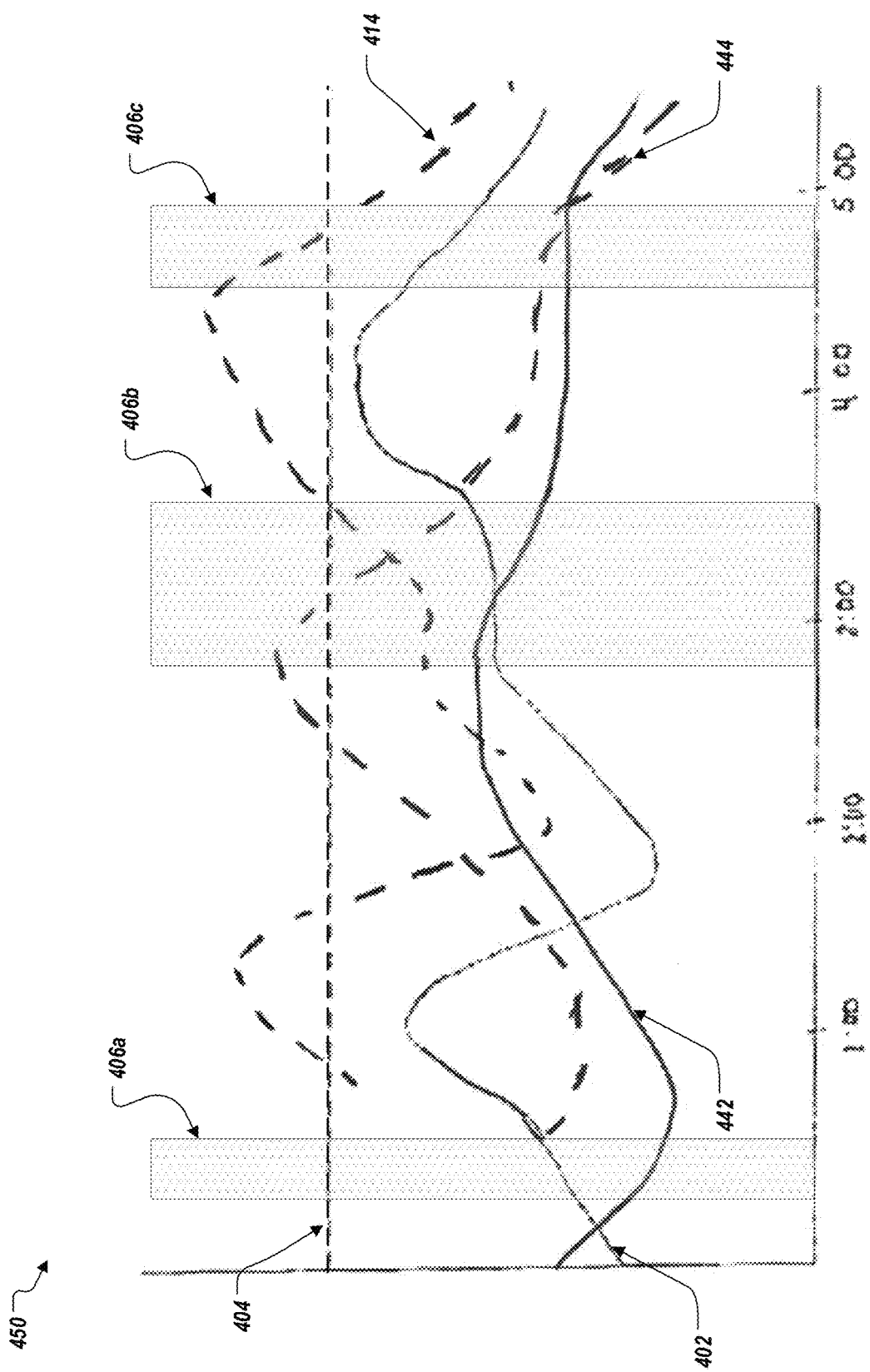

Based on the measured fatigue indicator values received for each flight crew member in step 310, an updated fatigue indicator profile for each of the flight crew members can be generated in step 312. Based on the updated fatigue indicator profiles, updated predicted fatigue profiles 414, 444 can be generated for each of the flight crew members in step 314, as depicted in FIG. 4F. These updated predicted fatigue profiles can then be compared to determine the appropriate mitigation intervention technique. For example, the updated predicted fatigue profile 450 includes updated predicted level of fatigue 414 for the pilot and an updated predicted level of fatigue 444 for the co-pilot, which can be used to determine whether either or both of the pilots is predicted to experience a fatigue level 414, 444 above the threshold fatigue 404 during one or more critical events 406. For example, as depicted in FIG. 4F, based on the updated predicted fatigue profile 450 for the pilot and co-pilot, the pilot is predicted to experience fatigue levels 414 above the threshold level 404 during the landing event 406c and the co-pilot is predicted to experience fatigue levels 444 above the threshold level 404 during the hazardous weather event 406b.

In some implementations, the flight risk mitigation interventions include comparing the updated predicted fatigue profiles of two or more flight crew members, and, based on this comparison, switching control of the aircraft from a first flight crew member to a second flight crew member. For example, if the updated predicted fatigue profile for a first flight crew member (e.g., the pilot) predicts that the first flight crew member will experience high fatigue levels during a critical portion of the flight, such as landing, and the updated predicted fatigue profile of a second flight crew member (e.g., the co-pilot) predicts that the second flight crew member will experience low levels of fatigue for the remainder of the flight, the flight risk mitigation interventions includes automatically switching control of the aircraft from the first flight crew member to the second flight crew member. For example, as depicted in FIG. 4F, based on the updated predicted fatigue profile 450 for the pilot and co-pilot, the pilot is predicted to experience fatigue levels 414 above the threshold level 404 during the landing event 406c and the co-pilot is predicted to experience fatigue level 444 below the threshold level 404 during the landing event 406c. In response, if the aircraft is being controlled by the pilot prior to the landing event 406c, the control of the aircraft will be automatically switched to the co-pilot during the time correlating to landing event 406c. Similarly, based on the updated predicted fatigue profile 450 for the pilot and co-pilot, the co-pilot is predicted to experience fatigue levels 444 above the threshold level 404 during the hazardous weather event 406b and the pilot is predicted to experience fatigue levels 414 below the threshold level 404 during the hazardous weather event 406b. In response, if the aircraft is being controlled by the co-pilot prior to the expected hazardous weather event 406b, the control of the aircraft will be automatically switched to the pilot during the times correlating to the hazardous weather event 406b.

In some implementations, the flight risk mitigation interventions include automatically engaging an autopilot function of the aircraft. In some implementations, if the updated predicted fatigue profile indicates high levels of fatigue for a first crew member and low levels of fatigue for a second crew member during a portion of the flight, a recommendation can be provided that the first crew member take a short rest or sleep while the second crew member flies the aircraft for the indicated portion of the flight.

In some implementations, the flight risk mitigation interventions include automatically rescheduling a different flight crew member for the flight. For example, if based on a predicted fatigue indicator profile generated for a first flight crew member, the first flight crew member is predicted to experience fatigue above a threshold level during a flight, the schedule of the first flight crew member can be automatically updated prior to the flight to remove the first flight crew member from the flight. In addition, a second flight crew member who, based on a predicted fatigue indicator profile generated for the second flight crew member, is predicted to have fatigue levels below the threshold fatigue throughout the duration of the flight can automatically be scheduled for the flight to replace the first flight crew member.

While processes 300, 306, and 340 are described as being executed by an onboard computing device (e.g., IRM computing device 150 of FIG. 2), it should be understood that all or portions of the processes 300, 306, and 340 can be performed by a server (e.g., server 102 of FIG. 2), a flight management system (e.g., flight management system 202 of FIG. 2), or other computing device(s) (e.g., computing devices 150a, 150b, 150c of FIG. 2). For example, data collected by the plurality of sensors can be provided to the server 102 in real time over the network 132 for processing of the data by the risk management application 144a stored on the server 102. In some implementations, a first portion of process 300 is performed by IRM computing device 150 and a second portion of process 300 is performed by the server 102. Further, processes 300, 306, and 340 are each described in relation to evaluating the risks associated with airline flights; however processes 300, 306, and 340 can be applicable to evaluating risks associated with other forms of transportation, such as motor vehicle or boat travel.

While this document contains many specific implementation details, these should not be construed as limitations on the scope of what can be claimed, but rather as descriptions of features that can be specific to particular implementations or embodiments. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features can be described above as acting in certain combinations and even initially claimed as such, one or more features from a claimed combination can, in some cases, be excised from the combination, and the claimed combination can be directed to a sub combination or variation of a sub combination.

In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other implementations are within the scope of the following claims.

A number of implementations of the present disclosure have been described. Nevertheless, it will be understood that various modifications can be made without departing from the spirit and scope of the present disclosure. Accordingly, other implementations are within the scope of the following claims.

The invention claimed is:

1. An in-flight risk management system comprising:
a microphone installed in a cockpit of an aircraft;
one or more in-flight risk management (IRM) computers in communication with the microphone; and
one or more data stores in communication with the one or more IRM computers and storing instructions that, when executed, cause the one or more IRM computers to perform operations comprising:
continuously monitoring audio data comprising cockpit conversations received from the microphone;
detecting, from the audio data, that a particular command litany has been initiated by processing, in real-time using a trained machine learning module, the audio data;
in response to detecting that the particular command litany has been initiated, determining, from the audio data and within the command litany, a command-response timing and a command-response accuracy, the command-response timing comprising a timing between responses and commands spoken during the particular command litany, and the command-response accuracy comprising an accuracy of the responses and commands spoken during the particular command litany; and
generating, based on the command-response timing and the command-response accuracy, one or more fatigue indicator values for each flight crew member involved in the particular command litany.

2. The system of claim 1, wherein detecting that the particular command litany has been initiated comprises processing, in real-time using the trained machine learning module, the audio data to detect an expected sequence of commands and responses associated with the particular command litany.

3. The system of claim 1, wherein detecting that the particular command litany has been initiated comprises detecting, in real-time using the trained machine learning module, the audio data to detect a trigger being spoken by a flight crew member, the trigger indicating the initiation of the particular command litany.

4. The system of claim 3, wherein the trigger comprises a first word of the particular command litany or a first phrase of the particular command litany.

5. The system of claim 3, wherein determining the command-response timing and the command-response accuracy comprises processing, in real-time using the trained machine learning module, audio data that proceeds the detected trigger.

6. The system of claim 1, wherein determining the command-response accuracy comprises processing, in real-time using the trained machine learning module, the audio data to determine whether an appropriate response to an initial command of the particular command litany has been provided by a flight crew member.

7. The system of claim 1, wherein determining the command-response timing comprises processing, in real-time using the trained machine learning module, the audio data to determine whether a flight crew member delays in providing an appropriate response to a detected command in the particular command litany.

8. The system of claim 1, wherein generating the one or more fatigue indicator values for each flight crew member involved in the particular command litany further comprises:
detecting, based on the audio data and within the command litany, a change in tone of a particular flight crew member involved in the particular command litany; and
generating, based on the detected change in tone, one or more measured fatigue indicator values for the particular flight crew member.

9. The system of claim 1, wherein the microphone is incorporated into a control panel of the aircraft.

10. The system of claim 1, wherein:
the in-flight risk management system further comprises one or more cameras; and
detecting that the particular command litany has been initiated comprises:
processing, in real-time using the trained machine learning module, image data generated by the one or more cameras to monitor actions of each flight crew member in the cockpit; and
detecting, based on processed image data, that a particular flight crew member has performed an action associated with initiation of the particular command litany.

11. The system of claim 1, wherein the operations further comprise, for each flight crew member involved in the particular command litany:
obtaining history information for a flight crew member;
obtaining flight information associated with a flight on which the flight crew member will be present;
determining, based on the history information and the flight information, a predicted fatigue profile for the flight crew member;
determining, based on the predicted fatigue profile for the flight crew member, a fatigue indicator profile for the flight crew member;
generating, based on one or more fatigue indicator values generated for the flight crew member, an updated fatigue indicator profile; and
generating, based on the updated fatigue indicator profile, an updated predicted fatigue profile.

12. The system of claim 11, wherein the fatigue indicator profile depicts an expected standard protocol command error rate for the respective flight crew member over a duration of a flight.

13. The system of claim 11, wherein the operations further comprise providing, based at least partly on the updated predicted fatigue profile, one or more flight risk mitigation interventions.

14. The system of claim 13, wherein providing one or more flight risk mitigation interventions comprises at least one of automatically rerouting the flight to an alternate landing location, automatically engaging an autopilot function of the aircraft, or directing control of the aircraft from a flight crew member to a remote operator.

15. A non-transitory computer-readable storage device storing software comprising instructions executable by one or more computers which, upon execution, cause the one or more computers to perform operations comprising:
- continuously monitoring audio data comprising cockpit conversations received from a microphone;
- detecting, from the audio data, that a particular command litany has been initiated by processing, in real-time using a trained machine learning module, the audio data;
- in response to detecting that the particular command litany has been initiated, determining, from the audio data and within the command litany, a command-response timing and a command-response accuracy, the command-response timing comprising a timing between responses and commands spoken during the particular command litany, and the command-response accuracy comprising an accuracy of the responses and commands spoken during the particular command litany; and
- generating, based on the command-response timing and the command-response accuracy, one or more fatigue indicator values for each flight crew member involved in the particular command litany.

16. The non-transitory computer-readable storage device of claim 15, wherein detecting that the particular command litany has been initiated comprises processing, in real-time using the trained machine learning module, the audio data to detect an expected sequence of commands and responses associated with the particular command litany.

17. The non-transitory computer-readable storage device of claim 15, wherein detecting that the particular command litany has been initiated comprises detecting, in real-time using the trained machine learning module, the audio data to detect a trigger being spoken by a flight crew member, the trigger indicating the initiation of the particular command litany.

18. The non-transitory computer-readable storage device of claim 15, wherein determining the command-response accuracy comprises processing, in real-time using the trained machine learning module, the audio data to determine whether an appropriate response to an initial command of the particular command litany has been provided by a flight crew member.

19. A computer-implemented method executed by one or more processors, the method comprising:
- continuously monitoring audio data comprising cockpit conversations received from a microphone;
- detecting, from the audio data, that a particular command litany has been initiated by processing, in real-time using a trained machine learning module, the audio data;
- in response to detecting that the particular command litany has been initiated, determining, from the audio data and within the command litany, a command-response timing and a command-response accuracy, the command-response timing comprising a timing between responses and commands spoken during the particular command litany, and the command-response accuracy comprising an accuracy of the responses and commands spoken during the particular command litany; and
- generating, based on the command-response timing and the command-response accuracy, one or more fatigue indicator values for each flight crew member involved in the particular command litany.

20. An in-flight risk management system comprising:
- a microphone installed in a cockpit of an aircraft;
- one or more in-flight risk management (IRM) computers in communication with the microphone; and
- one or more data stores in communication with the one or more IRM computers and storing instructions that, when executed, cause the one or more IRM computers to perform operations comprising:
  - continuously monitoring audio data comprising cockpit conversations received from the microphone;
  - detecting, from the audio data, that a particular command litany has been initiated;
  - in response to detecting that the particular command litany has been initiated, determining, from the audio data and within the command litany, a command-response timing and a command-response accuracy, the command-response timing comprising a timing between responses and commands spoken during the particular command litany, and the command-response accuracy comprising an accuracy of the responses and commands spoken during the particular command litany; and
  - generating, based on the command-response timing and the command-response accuracy, one or more fatigue indicator values for each flight crew member involved in the particular command litany, wherein generating the one or more fatigue indicator values for each flight crew member involved in the particular command litany further comprises:
    - detecting, based on the audio data and within the command litany, a change in tone of a particular flight crew member involved in the particular command litany; and
    - generating, based on the detected change in tone, one or more measured fatigue indicator values for the particular flight crew member.

21. A non-transitory computer-readable storage device storing software comprising instructions executable by one or more computers which, upon execution, cause the one or more computers to perform operations comprising:
- continuously monitoring audio data comprising cockpit conversations received from a microphone;
- detecting, from the audio data, that a particular command litany has been initiated;
- in response to detecting that the particular command litany has been initiated, determining, from the audio data and within the command litany, a command-response timing and a command-response accuracy, the command-response timing comprising a timing between responses and commands spoken during the particular command litany, and the command-response accuracy comprising an accuracy of the responses and commands spoken during the particular command litany; and
- generating, based on the command-response timing and the command-response accuracy, one or more fatigue indicator values for each flight crew member involved in the particular command litany, wherein generating the one or more fatigue indicator values for each flight crew member involved in the particular command litany further comprises:
  - detecting, based on the audio data and within the command litany, a change in tone of a particular flight crew member involved in the particular command litany; and
  - generating, based on the detected change in tone, one or more measured fatigue indicator values for the particular flight crew member.

22. A computer-implemented method executed by one or more processors, the method comprising:
  continuously monitoring audio data comprising cockpit conversations received from a microphone;
  detecting, from the audio data, that a particular command litany has been initiated;
  in response to detecting that the particular command litany has been initiated, determining, from the audio data and within the command litany, a command-response timing and a command-response accuracy, the command-response timing comprising a timing between responses and commands spoken during the particular command litany, and the command-response accuracy comprising an accuracy of the responses and commands spoken during the particular command litany; and
  generating, based on the command-response timing and the command-response accuracy, one or more fatigue indicator values for each flight crew member involved in the particular command litany, wherein generating the one or more fatigue indicator values for each flight crew member involved in the particular command litany further comprises:
    detecting, based on the audio data and within the command litany, a change in tone of a particular flight crew member involved in the particular command litany; and
    generating, based on the detected change in tone, one or more measured fatigue indicator values for the particular flight crew member.

* * * * *